(12) United States Patent
Gharbaoui et al.

US007812159B2

(10) Patent No.: US 7,812,159 B2
(45) Date of Patent: Oct. 12, 2010

(54) PROCESSES FOR PREPARING AROMATIC ETHERS

(75) Inventors: Tawfik Gharbaoui, Escondido, CA (US); John R. Fritch, Ramona, CA (US); Ashwin M. Krishnan, San Diego, CA (US); Beverly Wolgast Throop, San Diego, CA (US); Naomi S. Kato, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 863 days.

(21) Appl. No.: 11/327,923

(22) Filed: Jan. 9, 2006

(65) Prior Publication Data

US 2006/0155129 A1 Jul. 13, 2006

Related U.S. Application Data

(60) Provisional application No. 60/642,627, filed on Jan. 10, 2005.

(51) Int. Cl.
*C07D 401/12* (2006.01)
*A61K 31/4545* (2006.01)
*A61K 31/506* (2006.01)
*A61P 3/06* (2006.01)
*A61P 3/10* (2006.01)

(52) U.S. Cl. ............... 544/318; 544/319; 546/194; 546/217; 514/269; 514/318; 514/327

(58) Field of Classification Search ............ 544/318, 544/319; 546/194, 217; 514/269, 318, 327
See application file for complete search history.

(56) References Cited

U.S. PATENT DOCUMENTS

| | | | |
|---|---|---|---|
| 3,503,963 A | 3/1970 | Schweizer et al. |
| 3,592,932 A | 7/1971 | Duerr et al. |
| 3,598,801 A | 8/1971 | Beffa et al. |
| 3,608,087 A | 9/1971 | Patchett et al. |
| 3,686,238 A | 8/1972 | Zaffaroni et al. |
| 3,690,834 A | 9/1972 | Goldstein et al. |
| 3,849,420 A | 11/1974 | Tong |
| 3,852,434 A | 12/1974 | Kahan et al. |
| 3,862,117 A | 1/1975 | Leverenz |
| 3,887,329 A | 6/1975 | Hegar et al. |
| 3,948,914 A | 4/1976 | Fischer |
| 3,966,744 A | 6/1976 | Goldstein et al. |
| 3,966,764 A | 6/1976 | Goldstein et al. |
| 3,975,384 A | 8/1976 | Narr et al. |
| 3,984,411 A | 10/1976 | Claverie et al. |
| 4,101,541 A | 7/1978 | Petitpierre et al. |
| 4,189,427 A | 2/1980 | Komorowski |
| 4,242,507 A | 12/1980 | Itoh et al. |
| 4,267,174 A | 5/1981 | Berger et al. |
| 4,273,870 A | 6/1981 | Mollering et al. |
| 4,275,148 A | 6/1981 | Endo et al. |
| 4,397,848 A | 8/1983 | Bosies et al. |
| 4,493,726 A | 1/1985 | Burdeska et al. |
| 4,517,183 A | 5/1985 | Bosies et al. |
| 4,643,995 A | 2/1987 | Engel et al. |
| 4,766,213 A | 8/1988 | Juraszyk et al. |
| 5,624,941 A | 4/1997 | Barth et al. |
| 5,691,364 A | 11/1997 | Buckman et al. |
| 5,849,759 A | 12/1998 | Arnaiz et al. |
| 5,948,786 A | 9/1999 | Fujiwara et al. |
| 5,962,479 A | 10/1999 | Chen |
| 6,008,234 A | 12/1999 | Kochanny et al. |
| 6,187,777 B1 | 2/2001 | Norman et al. |
| 6,191,149 B1 | 2/2001 | Chokai et al. |
| 6,218,431 B1 | 4/2001 | Schoen et al. |
| 6,239,126 B1 | 5/2001 | Kelly et al. |
| 6,414,002 B1 | 7/2002 | Cheng et al. |
| 6,525,064 B1 | 2/2003 | Dellaria et al. |
| 6,545,016 B1 | 4/2003 | Dellaria et al. |
| 6,545,017 B1 | 4/2003 | Dellaria et al. |
| 6,583,154 B1 | 6/2003 | Norman et al. |
| 6,844,351 B1 | 1/2005 | Chen et al. |
| 6,956,047 B1 | 10/2005 | Chen et al. |
| 7,083,933 B1 | 8/2006 | Griffin |
| 7,132,426 B2 | 11/2006 | Jones et al. |
| 7,470,699 B2 * | 12/2008 | Jones et al. ............ 514/269 |
| 2005/0070562 A1 | 3/2005 | Jones et al. |
| 2005/0197353 A1 | 9/2005 | Ritzeler et al. |

(Continued)

FOREIGN PATENT DOCUMENTS

AT 327605 2/1976

(Continued)

OTHER PUBLICATIONS

Abdalla et al., "Synthesis and reaction of 3-cyano 2-(1H)-pyridones", *Pakistan Journal of Scientific and Industrial Research*, 20(3):139-49 (1977).

(Continued)

*Primary Examiner*—Venkataraman Balasubramanian
(74) *Attorney, Agent, or Firm*—Fish & Richardson P.C.; Lyle Spruce

(57) ABSTRACT

The present invention relates to processes for preparing aromatic ether compounds that are modulators of glucose metabolism and therefore useful in the treatment of metabolic disorders such as diabetes and obesity.

43 Claims, No Drawings

U.S. PATENT DOCUMENTS

| | | |
|---|---|---|
| 2006/0217379 A1 | 9/2006 | Jones et al. |
| 2007/0066590 A1 | 3/2007 | Jones et al. |
| 2007/0167473 A1 | 7/2007 | Jones et al. |

FOREIGN PATENT DOCUMENTS

| | | |
|---|---|---|
| AU | 492126 | 11/1975 |
| BE | 829845 | 12/1975 |
| BE | 868796 | 1/1979 |
| CH | 560197 | 3/1975 |
| DE | 2048375 | 4/1971 |
| DE | 2223644 | 11/1972 |
| DE | 2356644 | 5/1974 |
| DE | 2341925 | 3/1975 |
| DE | 2460238 A1 | 7/1975 |
| DE | 2503136 | 7/1975 |
| DE | 2831850 | 2/1980 |
| DE | 3334455 | 9/1984 |
| DE | 3406329 | 8/1985 |
| DE | 3601196 A1 | 7/1987 |
| DE | 19602095 | 7/1997 |
| DE | 19737723 | 2/1999 |
| DE | 19962936 | 6/2001 |
| EP | 0014976 | 9/1980 |
| EP | 0055693 | 7/1982 |
| EP | 0149088 | 7/1985 |
| EP | 0154190 | 9/1985 |
| EP | 0191603 | 8/1986 |
| EP | 0193249 | 9/1986 |
| EP | 0283261 | 9/1988 |
| EP | 0324426 | 7/1989 |
| EP | 0518675 A2 | 12/1992 |
| EP | 0556889 A1 | 8/1993 |
| EP | 0565488 | 10/1993 |
| EP | 0604800 | 7/1994 |
| EP | 0667343 | 8/1995 |
| EP | 0801059 | 10/1997 |
| EP | 0857483 A1 | 8/1998 |
| EP | 0940387 A1 | 9/1999 |
| EP | 1040831 | 10/2000 |
| EP | 1074549 | 2/2001 |
| EP | 1287133 | 3/2003 |
| EP | 1340749 | 9/2003 |
| EP | 1475094 | 11/2004 |
| FR | 1551400 | 12/1968 |
| GB | 935595 | 8/1963 |
| GB | 1250624 | 10/1971 |
| GB | 1311956 | 3/1973 |
| GB | 1393993 | 5/1975 |
| GB | 1493380 | 11/1977 |
| GB | 1495665 | 12/1977 |
| GB | 20010117899 | 7/2001 |
| JP | 55017382 | 2/1980 |
| JP | 61057587 | 3/1986 |
| JP | 5333599 | 12/1993 |
| JP | 0753546 | 2/1995 |
| JP | 11193277 | 7/1999 |
| JP | 2000038350 | 2/2000 |
| JP | 2001089452 | 4/2001 |
| JP | 269468 | 9/2004 |
| JP | 269469 | 9/2004 |
| NL | 6614961 | 4/1967 |
| NL | 6814810 | 4/1969 |
| RU | 938559 | 11/1993 |
| RU | 2067978 | 10/1996 |
| RU | 2119917 | 10/1998 |
| RU | 2153495 | 7/2000 |
| RU | 2158258 | 10/2000 |
| RU | 2198879 | 2/2003 |
| RU | 2200734 | 3/2003 |
| WO | WO9201697 | 2/1992 |
| WO | WO9407858 | 4/1994 |
| WO | WO 94/13677 | 6/1994 |
| WO | WO 95/33750 | 12/1995 |
| WO | WO 96/28427 | 9/1996 |
| WO | WO 96/32383 | 10/1996 |
| WO | WO 96/33994 | 10/1996 |
| WO | WO9633980 | 10/1996 |
| WO | WO 96/36613 | 11/1996 |
| WO | WO 97/08152 | 3/1997 |
| WO | WO 97/26252 | 7/1997 |
| WO | WO 97/29109 | 8/1997 |
| WO | WO97/40832 | 11/1997 |
| WO | WO 97/49706 | 12/1997 |
| WO | WO9748696 | 12/1997 |
| WO | WO 98/04528 | 2/1998 |
| WO | WO 98/08846 | 3/1998 |
| WO | WO 98/08847 | 3/1998 |
| WO | WO 98/11094 | 3/1998 |
| WO | WO9813354 | 4/1998 |
| WO | WO98/19998 | 5/1998 |
| WO | WO 98/47874 | 10/1998 |
| WO | WO 98/47903 | 10/1998 |
| WO | WO 99/09026 | 2/1999 |
| WO | WO 99/51599 | 10/1999 |
| WO | WO 00/11003 | 3/2000 |
| WO | WO 00/27825 | 5/2000 |
| WO | WO 00/31068 | 6/2000 |
| WO | WO 00/34241 | 6/2000 |
| WO | WO 00/35875 | 6/2000 |
| WO | WO 00/35886 | 6/2000 |
| WO | WO0055153 | 9/2000 |
| WO | WO 01/22938 | 4/2001 |
| WO | WO 01/23387 | 4/2001 |
| WO | WO 01/23388 | 4/2001 |
| WO | WO 01/25210 | 4/2001 |
| WO | WO 01/27107 | 4/2001 |
| WO | WO 01/47887 | 7/2001 |
| WO | WO 01/49677 | 7/2001 |
| WO | WO 01/53263 | 7/2001 |
| WO | WO 01/58900 | 8/2001 |
| WO | WO 01/62233 | 8/2001 |
| WO | WO 01/85699 | 11/2001 |
| WO | WO0190082 | 11/2001 |
| WO | WO 02/02549 | 1/2002 |
| WO | WO 02/06237 | 1/2002 |
| WO | WO 02/06274 | 1/2002 |
| WO | WO 02/19975 | 3/2002 |
| WO | WO 02/32893 | 4/2002 |
| WO | WO 02/40451 | 5/2002 |
| WO | WO 02/40456 | 5/2002 |
| WO | WO 02/40458 | 5/2002 |
| WO | WO 02/40480 | 5/2002 |
| WO | WO 02/44362 | 6/2002 |
| WO | WO 02/059083 | 8/2002 |
| WO | WO 02/070485 | 9/2002 |
| WO | WO 02/072101 | 9/2002 |
| WO | WO 02/085892 | 10/2002 |
| WO | WO 02/098864 | 12/2002 |
| WO | WO 02/098878 | 12/2002 |
| WO | WO 03/000666 | 1/2003 |
| WO | WO 03/002544 | 1/2003 |
| WO | WO 03/004498 | 1/2003 |
| WO | WO 03/018556 | 3/2003 |
| WO | WO 03/026661 | 4/2003 |
| WO | WO 03/032989 | 4/2003 |
| WO | WO 03/050117 | 6/2003 |
| WO | WO 03/057689 | 7/2003 |
| WO | WO 03/077656 | 9/2003 |
| WO | WO 03/087064 | 10/2003 |
| WO | WO 03/094845 | 11/2003 |
| WO | WO 04/000819 | 12/2003 |
| WO | WO 04/000843 | 12/2003 |
| WO | WO 2004/009596 | 1/2004 |

| WO | WO 2004/009597 | 1/2004 |
| WO | WO 2004/009602 | 1/2004 |
| WO | WO 2004/024943 | 3/2004 |
| WO | WO 2004/029204 | 4/2004 |
| WO | WO 2004/031189 | 4/2004 |
| WO | WO 2004/035588 | 4/2004 |
| WO | WO 2004/041164 | 5/2004 |
| WO | WO 2004/056825 | 7/2004 |
| WO | WO 2004/056829 | 7/2004 |
| WO | WO 2004/062665 | 7/2004 |
| WO | WO 2004/065380 | 8/2004 |
| WO | WO 2004/074218 | 9/2004 |
| WO | WO 2004/076413 | 9/2004 |
| WO | WO 2004/099144 | 11/2004 |
| WO | WO 2004/111000 | 12/2004 |
| WO | WO 2005/007647 | 1/2005 |
| WO | WO 2005007647 A1 * | 1/2005 |
| WO | WO 2005/016894 | 2/2005 |
| WO | WO 2005/020920 | 3/2005 |
| WO | WO 2005/023762 | 3/2005 |
| WO | WO 2005/025554 | 3/2005 |
| WO | WO 2005/026148 | 3/2005 |
| WO | WO 2005/030127 | 4/2005 |
| WO | WO 2005/030129 | 4/2005 |
| WO | WO 2005/030751 | 4/2005 |
| WO | WO 2005/033099 | 4/2005 |
| WO | WO 2005/035525 | 4/2005 |
| WO | WO 2005/037215 | 4/2005 |
| WO | WO 2005/040095 | 5/2005 |
| WO | WO 2005/042488 | 5/2005 |
| WO | WO 2005/046603 | 5/2005 |
| WO | WO 2005/047297 | 5/2005 |
| WO | WO 2005/049033 | 6/2005 |
| WO | WO 2005/058315 | 6/2005 |
| WO | WO 2005/058849 | 6/2005 |
| WO | WO 2005/061489 | 7/2005 |
| WO | WO 2005/063750 | 7/2005 |
| WO | WO 2005/072530 | 8/2005 |
| WO | WO 2005/075426 | 8/2005 |
| WO | WO 2005/090348 | 9/2005 |
| WO | WO 2005/100365 | 10/2005 |
| WO | WO 2005/117909 | 12/2005 |
| WO | WO 2005/121121 | 12/2005 |
| WO | WO 2006/040966 | 4/2006 |
| WO | WO 2006/043490 | 4/2006 |
| WO | WO 2006/067531 | 6/2006 |
| WO | WO 2006/067532 | 6/2006 |
| WO | WO 2006/070208 | 7/2006 |

OTHER PUBLICATIONS

Abramovitch et al., "Solution and flash vacuum pyrolysis of some 2,6-disubstituted β-phenethylsulfonyl azides and of β-styrenesulfonyl azide", J. Org. Chem., 50:2066-73 (1985).
Abstract #107, p. 56, *Toward Understanding Islet Biology*, Jan. 21, 2003-Jan. 26, 2003, Keystone, Colorado.
Abstract #112, p. 42, *Diabetes Mellitus: Molecular Mechanisms, Genetics and New Therapies*, Jan. 27, 2005-Feb. 2, 2005, Keystone, Colorado.
Abstract #228, p. 54, *Diabetes Mellitus: Molecular Mechanisms, Genetics and New Therapies*, Jan. 27, 2005-Feb. 2, 2005, Keystone, Colorado.
Abstract #117 & Poster, *Diabetes: Molecular Genetics, Signaling Pathways and Integrated Physiology*, Jan. 14, 2007-Jan. 19, 2007, Keystone, Colorado.
Abstract #230 & Poster, *Diabetes: Molecular Genetics, Signaling Pathways and Integrated Physiology*, Jan. 14, 2007-Jan. 19, 2007, Keystone, Colorado.
Accession No. 2003:2415108 CHEMCATS, Interbioscreen Compound Library, Chemical Name: 1H-Pyrazolo[3,4-d]pyrimidine-4-amine, N-cyclohexyl-N-methyl-1-(3-methylphenyl)-, XP-002311326, 2003, CAS Registry No. 393844-90-1.
Accession No. 2003:2415906 CHEMCATS, Interbioscreen Compound Library, Chemical Name: 1H-Pyrazolo[3,4-d]pyrimidine-4-amine, N-cyclohexyl-1-(4-methylphenyl)-N-methyl-, XP-002311325, 2003, CAS Registry No. 393844-89-8.
Accession No. 2003:2416398 CHEMCATS, Interbioscreen Compound Library, Chemical Name: 1H-Pyrazolo[3,4-d]pyrimidine-4-amine, N-cyclohexyl-1-(2,4-dimethylphenyl)-N-methyl-, XP-002311324, 2003, CAS Registry No. 393844-91-2.
Accession No. 2003:2417080 CHEMCATS, Interbioscreen Compound Library, Chemical Name: 1H-Pyrazolo[3,4-d]pyrimidine-4-amine, N-cyclohexyl-N-methyl-1-phenyl-), XP-002311323, 2003, CAS Registry No. 393844-87-6.
Appukkuttan et al., "Transition-metal-free Sonogashira-type coupling reactions in water", *European Journal of Organic Chemistry*, 24:4713-6 (2003).
Arvanitis et al., "CRF ligands via Suzuki and Negishi couplings of 3-pyridyl boronic acids or halides with 2-benzyloxy-4-chloro-3-nitropyridine", *Bioorganic & Medicinal Chemistry Letters*, 13(2):289-91 (2003).
Arvanitis et al., "Imidazo[4,5-b]pyridines as corticotropin releasing factor receptor ligands", *Bioorganic & Medicinal Chemistry Letters*, 13(1):125-8 (2003).
Arvanitis et al., "Non-peptide corticotropin-releasing hormone antagonists: syntheses and structure-activity relationships of 2-anilinopyrimidines and -triazines", *J. Med. Chem.*, 42(5):805-18 (1999).
Arvanitis et al., "Non-peptide corticotropin-releasing hormone antagonists: syntheses and structure-activity relationships of 2-anilinopyrimidines and -triazines", *J. Med. Chem.*, Supporting Material pp. 1-10 (1999).
Arvela et al., "Rapid cyanation of aryl iodides in water using microwave promotion", *Org. Biomol. Chem.*, 1:1119-21 (2003).
Arvela et al., "Rapid, easy cyanation of aryl bromides and chlorides using nickel salts in conjunction with microwave promotion", *J. Org. Chem.*, 68:9122-5 (2003).
Baindur et al., "Solution-phase synthesis of a library of 3,5,7-trisubstituted 3H-[1,2,3]triazolo[4,5-d]pyrimidines", *J. Comb. Chem.*, 5:653-9 (2003).
Bakkestuen et al., "Regioselective N-9 arylation of purines employing arylboronic acids in the presence of Cu(II)", *Tetrahedron Letters*, 44:3359-62 (2003).
Baraldi et al., "An efficient one-pot synthesis of 6-alkoxy-8,9-dialkylpurines via reaction of 5-amino-4-chloro-6-alkylaminopyrimidines with N,N-dimethylalkaneamides and alkoxide ions", *Tetrahedron*, 58:7607-11 (2002).
Barta et al., "Synthesis and activity of selective MMP inhibitors with an aryl backbone", *Bioorg. & Med. Chem. Ltrs.*, 10(24):2815-7 (2000).
Baskin et al., "A mild, convenient synthesis of sulfinic acid salts and sulfonamides from alkyl and aryl halides", *Tetrahedron Letters*, 43:8479-83 (2002).
Baskin et al., "An efficient copper catalyst for the formation of sulfones from sulfinic acid salts and aryl iodides", *Org. Lett.*, 4(25):4423-5 (2002).
Baskin et al., "An efficient copper catalyst for the formation of sulfones from sulfinic acid salts and aryl iodides", *Org. Lett.*, 4(25):4423-5 (2002) Supporting Material #1.
Baskin et al., "An efficient copper catalyst for the formation of sulfones from sulfinic acid salts and aryl iodides", *Org. Lett.*, 4(25):4423-5 (2002) Supporting Material #2.
Bedford et al., "Nonquaternary cholinesterase reactivators. 3. 3(5)-substituted 1,2,4-oxadiazol-5(3)-aldoximes and 1,2,4-oxadiazole-5(3)-thiocarbohydroximates as reactivators of organophosphonate-inhibited eel and human acetylcholinesterase in vitro", *J. Med. Chem.*, 29(11):2174-83 (1986).
Beller et al., "Base-catalyzed amination of olefins: an example of an environmentally friendly synthesis of amines", *Chemosphere*, 43(1):21-6 (2001).
Berge et al., "Pharmaceutical salts", *Journal of Pharmaceutical Sciences*, 66(1):1-19 (1977).
Betti et al., "Novel 3-aralkyl-7-(amino-substituted)-1,2,3-triazole[4,5-d]pyrimidines with high affinity toward A1 adenosine receptors", *J. Med. Chem.*, 41:668-73 (1998).

Biagi et al., "Synthesis of 4,6-disubstituted- and 4,5,6-trisubstituted 2-phenylpyrimidines and their affinity towards $a_1$ adenosine receptors", *Il Farmaco*, 52(1):61-5 (1997).

Boldt et al., "Simple Synthesis of 2,4-diaminopyridines", *Angewandte Chemie International Edition*, 9(5):377 (1970).

Bomika et al., translation of "Certain reactions of nucleophilic substitution of 2-chloro-3-cyanopyridines", *Khimiya Geterotsiklicheskikh Soedinenii*, 8:1085-8 (1976)(Translated pp. 896-899).

Boschelli et al., "1,3,4-oxadiazole, 1,3,4-thiadiazole, and 1,2,4-triazole analogs of the fenamates: in vitro inhibition of cyclooxygenase and 5-lipoxygenase activities", *J. Med. Chem.*, 36:1802-10 (1993).

Boswell et al., "Synthesis of some N-carboxylic acid derivatives of 3-phenoxypyrrolidines, 4-phenoxypiperidines, and 3-phenoxynortropanes with muscle relaxant and anticonvulsant activities", *J. Med. Chem.*, 17(9):1000-8 (1974).

Brancati et al., "Body weight patterns from 20 to 49 years of age and subsequent risk for diabetes mellitus: the Johns Hopkins precursors study", *Arch. Intern. Med.*, 159:957-63 (1999).

Bromidge et al., "Design of [R-(Z)]-(+)-alpha-(methoxyimino)-1-azabicyclo[2.2.2]octane-3-acetonitrile (SB 202026), a functionally selective azabicyclic muscarinic M1 agonist incorporating the N-methoxy imidoyl nitrile group as a novel ester bioisostere", *J. Med. Chem.*, 40(26):4265-80 (1997).

Buehler et al., "Physiologically active compounds. VI. Cyclic amino thiolesters of substituted chloroacetic, benzilic and glycolic acids", *J. Med. Chem.*, 8:643-7 (1965).

Bulger et al., "An investigation into the alkylation of 1,2,4-triazole", *Tetrahedron Letters*, 41:1297-1301 (2000).

Chan et al., "Isoquinoline-6-carboxamides as potent and selective anti-human cytomegalovirus (HCMV) inhibitors", *Bioorganic & Medicinal Chemistry Letters*, 9:2583-6 (1999).

Chen et al., "Design and synthesis of a series of non-peptide high-affinity human corticotropin-releasing factor$_1$ receptor antagonists", *J. Med. Chem.*, 39:4358-60 (1996).

Chen et al., "Free radical method for the synthesis of spiro-piperidinyl heterocycles", *Tetrahedron Letters*, 37(30):5233-4 (1996).

Chen et al., "Optimization of 3-phenylpyrazolo[1,5-α]pyrimidines as potent corticotropin-releasing factor-1 antagonists with adequate lipophilicity and water solubility", *Bioorganic & Medicinal Chemistry Letters*, 14:3669-73 (2004).

Chorvat et al., "Synthesis, corticotropin-releasing factor receptor binding affinity, and pharmacokinetic properties of triazolo-, imidazo-, and pyrrolopyrimidines and -pyridines", *J. Med. Chem.*, 42:833-48 (1999).

Chu et al., "A role for β-cell-expressed G protein-coupled receptor 119 in glycemic control by enhancing glucose-dependent insulin release," *Endocrinology* (2007) 148:2601-2609.

Chu et al., "A role for Intestinal Endocrine Cell-Expressed GPR119 in Glycemic Control by Enhanching GLP-1 and GIP Release", Arena Pharmaceuticals pre-publication document.

Clark et al., "Synthesis and analgesic activity of 1,3-dihydro-3-(substituted phenyl)imidazo[4,5-b]pyridin-2-ones and 3-(substituted phenyl)-1,2,3-triazolo[4,5-b]pyridines", *J. Med. Chem.*, 21(9):965-78 (1978).

Cocuzza et al., "Use of the suzuki reaction for the synthesis of aryl-substituted heterocycles as corticotropin-releasing hormone (CRH) antagonists", *Bioorganic & Medicinal Chemistry Letters*, 9:1063-6 (1999).

Cohen et al., "The preparation and properties of 6-halomethylpurines", Div. of Nucleoprotein Chemistry, Sloan-Kettering Institute for Cancer Research, and Sloan Kettering Div. Grad. School of Med. Sci., Cornell Univ. Med. College, 27:3545-9 (1962).

Colandrea et al., "Synthesis and regioselective alkylation of 1,6- and 1,7-naphthridines", *Tetrahedron Letters*, 41:8053-7 (2000).

Collier et al., "Radiosynthesis and in-vivo evaluation of the pseudopeptide σ-opioid antagonist [$^{125}$I]ITIPP(ψ)", *J. Labeled Compd. Radiopharm.*, 42(Suppl. 1):S264-S266 (1999).

Cossey et al., "Amide-acid chloride adducts. VI. Pyridines and pyridinium salts from cyanoacetamides", *Australian Journal of Chemistry*, 29(5):1039-50 (1976).

Cover Sheet and 1185 Compounds—CAS Registry and ChemCats files (391pp.), 2005.

Cover Sheet and 18 Compounds—CAS Registry file (9 pp.), 2004.

Cover Sheet and 2534 Compounds—CAS Registry and ChemCats file (817pp.), 2006.

Cover Sheet and 54 Compounds—CAS Registry file (23 pp.), 2001.

23 Compounds-ChemCats File (11pp.), 2003.

Cryan et al., "Behavioral characterization of the novel GABA$_B$ receptor-positive modulator GS39783 (N,N'-dicyclopentyl-2-methylsulfanyl-5-nitro-pyrimidine-4,6-diamine): anxiolytic-like activity without side effects associated with baclofen or benzodiazepines", *Journal of Pharmacology and Experimental Therapeutics*, 310(3):952-63 (2004).

Dai et al., "The first general method for palladium-catalyzed Negishi cross-coupling of aryl and vinyl chlorides: use of commercially available Pd(P(t-Bu)$_3$)$_2$ as a catalyst", *J. Am. Chem. Soc.*, 123(12):2719-24 (2001).

Desimoni et al., "Polynuclear isoxazole types-I isoxazolo[4,5-d]pyrimidines$^1$", *Tetrahedron*, 23:675-80 (1967).

Devita et al., "Identification and initial structure-activity relationships of a novel non-peptide quinolone GnRH receptor antagonist", *Bioorg. & Med. Chem. Ltrs.*, 9(17):2615-20 (1999).

Di Braccio et al., "Synthesis and preliminary pharmacological examination of 2,4-disubstituted N,N-dialkyl-1,8-naphthyridine-3-carboxamides", *Farmaco*, 44(9):865-81 (1989).

Dzierba et al., "Synthesis, structure-activity relationships, and in vivo properties of 3,4-dihydro-1H-pyrido[2,3-b]pyrazin-2-ones as corticotropin-releasing factor-1 receptor antagonists", *Journal of Medicinal Chemistry*, 47(23):5783-90 (2004).

Eicher et al., "Reaction of triafulvenes with isonitriles, a simple synthesis of diphenyl-substituted functionalized cyclobutene derivatives and related products", *Synthesis*, 7:619-26 (1987).

Escher et al., "Cyclopentylamine substituted triazolo[4,5-D]pyrimidine: implications for binding to the adenosine receptor", *Tetrahedron Letters*, 32(29):3583-4 (1991).

Fyfe et al., *Diabetes* (2007) 56(Supplement 1):A142 (Abstract #532-P).

Gangloff et al., "Synthesis of 3,5-disubstituted-1,2,4-oxadiazoles using tetrabutylammonium fluoride as a mild and efficient catalyst", *Tetrahedron Letters*, 42:1441-3 (2001).

Gilligan et al., "Corticotropin releasing factor (CRF) receptor modulators progress and opportunities for new therapeutic agents", *J. Med. Chem.*, 43(9):1641-60 (2000).

Gilligan et al., "Corticotropin-releasing factor antagonists: recent advances and exciting prospects for the treatment of human diseases", *Current Opinion in Drug Discovery & Development*, 7(4):487-97 (2004).

Giner-Sorolla et al., "The synthesis and properties of 6-mercaptomethylpurine and derivatives", *Cornell University Medical College*, 8:667-72 (1965).

Goldner et al., "Die Darstellung 2,9-; 2,6,9- und 6,9-substituierter purine", *Journal fuer praktische chemie* (Leipzig) 12:242-52 (1961).

Gomtsyan et al., "Design, synthesis, and structure-activity relationship of 6-alkynylpyrimidines as potent adenosine kinase inhibitors", *J. Med. Chem.*, 45(17):3639-48 (2002).

Greene et al., *Protective Groups in Organic Synthesis*, 3$^{rd}$ Ed., John Wiley & Sons, New York (1999).

Gröger, "Modern Methods of the Suzuki Cross Coupling: the Long Expected General Synthetic Routes Using Aryl Chlorides", Groger, Harald, *Journal Fuer Praktische Chemie*, 342(4):334-9 (2000).

Guillory, K.J., "Generation of Polymorphs, Hydrates, Solvates, and Amorphous Solids," in: *Polymorphism in Pharmaceutical Solids*, vol. 95, pp. 202-209 1999.

Hamada et al., "An improved synthesis of arylsulfonyl chlorides from aryl halides", *Synthesis* pp. 852-854 (1986).

He et al., "4-(1,3-dimethozyprop-2-ylamino)-2,7-dimethyl-8-(2,4-dichlorophenyl)-pyrazolo[1,5-a]-1,3,5-triazine: a potent, orally bioavailable CRF$_1$ receptor antagonist", *J. Med. Chem.*, 43:449-56 (2000).

Hecht et al., "On the activation of cytokins", *J. of Biological Chemistry*, 250(18):7343-51 (1975).

Hersperger et al., "Palladium-catalyzed cross-coupling reactions for the synthesis of 6,8-disubstituted 1,7-naphthyridines: a novel class of potent and selective phosphodiesterase type 4D inhibitors", *J. Med. Chem.*, 43:675-82 (2000).

Higuchi et al., "Pro-drugs as novel delivery systems", A.C.S. Symposium Series, vol. 14 (1987).

Hill et al., "Environmental contributions to the obesity epidemic", *Science*, 280(5368):1371-4 (1998).

Hocek et al., "An efficient synthesis of 2-substituted 6-methylpurine bases and nucleosides by Fe- or Pd-catalyzed cross-coupling reactions of 2,6-dichloropurines", *J. Org. Chem.*, 68:5773-6 (2003).

Huang et al., "Synthesis and antiplatelet activity of phenyl quinolones", *Bioorganic & Medicinal Chemistry*, 6:1657-62 (1998).

Jia et al., "Design, synthesis and biological activity of novel non-amidine factor Xa inhibitors. Part 1: $P_1$ structure-activity relationships of the substituted 1-(2-Naphthyl)-1H-pyrazole-5-carboxylamides", *Bioorganic & Medicinal Chemistry Letters*, 12:1651-5 (2002).

Jogie et al., "Unusual protein-binding specificity and capacity of aza-arenophilic gels", *Journal of Molecular Recognition*, 11:261-2 (1998).

Jones et al., CAPLUS Abstract 142:176857 (2005).

Kawase et al., "α-trifluoromethylated acyloins induce apoptosis in human oral tumor cell lines", *Bioorg. & Med. Chem. Ltrs.*, 9(21):3113-8 (1999).

Kelley et al., "Benzodiazepine receptor binding activity of 8-substituted-9-(3-substituted-benzyl)-6-(dimethylamino)-9H-purines", *J. Med. Chem.*, 33(1):196-202 (1990).

Kelly et al., "A synthesis of aaptamine", *Tetrahedron*, 41(15):3033-66 (1985).

Kempson et al., "Fused pyrimidine based inhibitors of phosphodiesterase 7 (PDE7): synthesis and initial structure-activity relationships", *Bioorganic & Medicinal Chemistry Letters*, 15:1829-33 (2005).

Khattab et al., "Quinolines with heteroatom substituents in position 2 and 4 nucleophilic substitution of 2,4-dichloro-3-phenylquinolines", *ACH—Models in Chemistry*, 131(3-4):521-7 (1994).

Klötzer et al., "Chlorierende formylierungsreaktionen an pyrimidinen", *Monatshefte fuer Chemie*, 96(5):1567-72 (1965).

Kotian et al., "Synthesis, ligand binding, and quantitative structure-activity relationship study of 3β-(4'-substituted phenyl)-2β-heterocyclic tropanes: evidence for an electrostatic interaction at the 2β-position", *J. Med. Chem.*, 39(14):2753-63 (1996).

Krauze et al., "Derivatives of 3-cyano-6-phenyl-4-(3'-pyridyl)-pyridine-2(1H)-thione and their neurotropic activity", *European Journal of Medicinal Chemistry*, 34(4):301-10 (1999).

Krauze et al., "Synthesis of 3-oxoisothiazolo[5,4-b]pyridines", *Khimiya Geterotsiklicheskikh Soedinenii*, 4:508-12 (1982).

Kumagai et al., "Synthesis, SAR and biological activities of $CRH_1$ receptor: novel 3- or 4-carbamoyl-1,2,5,6-tetrahydropyridinopyrrolopyrimidine derivative", 4$^{th}$ ACS National Meeting, Aug. 18-22, 2002, Boston, MA Poster #259.

Lai et al., "A one-pot method for the efficient conversion of aryl- and acyl-substituted methyl alcohols into chlorides", *Synthetic Communications*, 33(10):1727-32 (2003).

Lanier et al., "Small molecule corticotropin-releasing factor antagonists", *Expert Opinion*, 12(11):1619-30 (2002).

Le Bas et al., "Radioiodinated analogs of EP 00652218 for the exploration of the tachykinin NK1 receptor by spect", *J. Labeled Compd. Radiopharm.*, 44:S280-S282 (2001).

Le Stunff et al., "Early changes in postprandial insulin secretion, not in insulin sensitivity, characterize juvenile obesity", *Diabetes*, 43:696-702 (1989).

Leadbeater et al., "First examples of transition-metal free sonogashira-type couplings", *Organic Letters*, 5(21):3919-22 (2003).

Leadbeater et al., "Transition-metal free sonogashira-type couplings", Department of Chemistry, King's College London, Supplementary Information, pp. S1-S4.

Lee et al., "Synthesis and biological evaluation of clitocine analogues as adenosine kinase inhibitors", *Bioorg. & Med. Chem. Ltrs.*, 11(18):2419-22 (2001).

Leese et al., "Potential antipurines. Part II. Synthesis of 6- and 9-substituted purines and 8-azapurines", *Journal of the Chemical Society*, pp. 4107-4110 (1958).

Lin et al., "Synthesis and antitumor activity of halogen-substituted 4-(3,3-dimethyl-1-triazeno)quinolines", *J. Med. Chem.*, 21(3):268-72 (1978).

Litvak et al., "Polynucleotides and their components in the processes of aromatic nucleophilic substitution: II. Nucleophilic modification of 3',5'-Bis-O-(α,β,α',β'-tetrafluoropyrid-γ-yl)thymidine", *Russian Journal of Bioorganic Chemistry*, 30(4):337-43 (2004).

Litvinov et al., "Naphthyridines. Structure, physicochemical properties and general methods of synthesis", *Russian Chemical Reviews*, 69(3):201-20 (2000).

Loupy et al., "Easy and efficient $S_NAr$ reactions on halopyridines in solvent free conditions", *Heterocycles*, 32(10):1947-52 (1991).

Luo et al., "Microwave-assisted synthesis of aminopyrimidines", *Tetrahedron Letters*, 43:5739-42 (2002).

Ma et al., "Mild method for Ullmann coupling reaction of amines and aryl halides", *Organic Letters*, 5(14):2453-5 (2003).

Macchia et al., "New N-n-propyl-substituted 3-aryl- and 3-cyclohexylpiperidines as partial agonists at the $D_4$ dopamine receptor", *J. Med. Chem.*, 46(1):161-8 (2003).

Mackman et al., "2-(2-hydroxy-3-alkoxyphenyl)-1H-benzimidazole-5-carboxamidine derivatives as potent and selective urokinase-type plasminogen activator inhibitors", *Bioorganic & Medicinal Chemistry Letters*, 12(15):2019-22 (2002).

Majeed et al., "Stannylation reactions and cross-couplings in pyrimidines", *Tetrahedron*, 45(4):993-1006 (1989).

Matsui et al., "Highly potent inhibitors of TNF-α production. Part II: metabolic stabilization of a newly found chemical lead and conformational analysis of an active diastereoisomer", *Bioorg. Med. Chem.*, 10(12):3787-805 (2002).

Matsuno et al., "Potent and selective inhibitors of platelet-derived growth factor receptor phosphorylation. 3. replacement of quinazoline moiety and improvement of metabolic polymorphism of 4-[4-(N-substituted (thio)carbamoyl)-1-piperazinyl]-6,7-dimethoxyquinazoline derivatives", *J. Med. Chem.*, 46(23):4910-25 (2003).

Mesguiche et al., "4-alkoxy-2,6-diaminopyrimidine derivatives: inhibitors of cyclin dependent kinases 1 and 2", *Bioorganic & Medicinal Chemistry Letters*, 13:217-22 (2003).

Metzger et al., Einstufensynthese von 2,4-Bis(sec-alkylamino-6-halogen-3-pyridincarbonitrilen), *Liebigs Annalen der Chemie*, 6:946-53 (1980).

Mittelbach et al., "Syntheses with nitriles. 60 (1). preparation of 4-amino-5-cyano-6-phenylpyrimidines from 2-amino-1,1-dicyano-2-phenylethene", *Journal of Heterocyclic Chemistry*, 17(7):1385-7 (1980).

Miyashita et al., "Preparation of heteroarenecarbonitriles by reaction of haloheteroarenes with potassium cyanide catalyzed by sodium p-toluenesulfinate", *Heterocycles*, 39(1):345-50 (1994).

Mohan et al., "Solid-phase synthesis of N-substituted amidinophenoxy pyridines as factor Xa inhibitors", *Bioorganic & Medicinal Chemistry Letters*, 8(14):1877-82 (1998).

Mombereau et al., "Genetic and pharmacological evidence of a role for $GABA_B$ receptors in the modulation of anxiety- and antidepressant-like behavior", *Neuropsychopharmacology*, 29(6):1050-62 (2004).

Mongin et al., "Advances in the directed metallation of azines and diazines (pyridines, pyrimidines, pyrazines, pyridazines, quinolines, benzodiazines and carbolines). Part 1: metallation of pyridines, quinolines and carbolines", *Tetrahedron*, 57(19):4059-90 (2001).

Montgomery et al., "Isonucleosides. I. Preparation of methyl 2-deoxy-2-(purin-9-yl)arabinofuranosides and methyl 3-deoxy-3-(purin-9-yl)xylofuranosides", *Journal of Organic Chemistry*, 40(13):1923-7 (1975).

Morimoto et al., "Potent and selective ET-A antagonists. 1. Syntheses and structure-activity relationships of N-(6-(2-(aryloxy)ethoxy)-4-pyrimidinyl)sulfonamide derivatives", *J. Med. Chem.*, 44(21):3355-68 (2001).

Moschitskii et al., translation of "Reaction of 2,3,5,6-tetrachloro-4-pyridyl-vinyl sulfone with nuleophilic agents", *Khimiya Geterotsiklicheskikh Soedinenii* (1972) pp. 1634-1637 (Translated pp. 1482-1485).
Muci et al., "Practical palladium catalysts for C-N and C-O bond formation", *Topics in Current Chemistry*, 219:131-209 (2002).
Müller et al., "7-Deaza-2-phenyladenines: structure-activity relationships of potent $A_1$ selective adenosine receptor antagonists", *J. Med. Chem.*, 33:2822-8 (1990).
Nakazato et al., "Design, synthesis and structure-affinity relationships of 4-methylidenepiperidine and 4-aryl-1,2,3,6-tetrahydropyridine derivatives as corticotropin-releasing factor$_1$ receptor antagonists", *Bioorganic & Medicinal Chemistry*, 8(5):1183-93 (2000).
Nakazato et al., "Synthesis, SAR and biological activities of $CRH_1$ Receptor: novel 3- or 4-carbamoyl-1,2,5,6-tetrahydropyridinoquinoline derivative", $24^{th}$ ACS National Meeting, Aug. 18-22, 2002, Boston, MA Poster #258.
Nesi et al., "New difunctionalized 4-nitroisoxazoles from α-nitroacetophenone oxime", *Heterocycles*, 23(6):1465-69 (1985).
Nicewonger et al., "Microwave-assisted acylation of 7-amino-5-aryl-6-cyanopyridol[2,3-d]pyrimidines", *Molecular Diversity*, 7(2-4):247-52 (2003).
Norman et al., "Structure-activity relationships of a series of pyrrolo(3,2-d)pyrimidine derivatives and related compounds as neuropeptide Y5 receptor antagonists", *J. Med. Chem.*, 43(22):4288-4312 (2000).
Norman et al., "Structure-activity relationships of a series of pyrrolo(3,2-d)pyrimidine derivatives and related compounds as neuropeptide Y5 receptor antagonists", *J. Med. Chem.*, 43(22):4288-312, JM000269T, Supplemental Material: 1-11 (2000).
Oae, *Organic chemistry of Sulfur, Ed.*, Plenum press new York, 1997.
Olesen et al., "The use of bioisosteric groups in lead optimization", *Current Opinion in Drug Discovery & Development*, 4(4):471-8 (2001).
Overton et al., "Deorphanization of a G protein-coupled receptor for oleoylethanolamide and its use in the discovery of small-molecule hypophagic agents," *Cell Metabolism* (2006) 3:167-175.
Parlow et al., "Design, synthesis, and crystal structure of selective 2-pyridone tissue factor VIIa inhibitors", *J. Med. Chem.*, 46(22):4696-701 (2003).
Paulsen et al., "Darstellung von Bausteinen zur Synthese carbocyclischer furanose-analoga", *Chemische Berichte*, (1981) 114(1):346-358.
Pedersen, "The impact of obesity on the pathogenesis of non-insulin-dependent diabetes mellitus: a review of current hypotheses", *Diab. Metab. Rev.*, 5(6):495-509 (1989).
Perry et al., "Prospective study of risk factors for development of non-insulin dependent diabetes in middle aged British men", *BMJ*, 310(6979):560-4 (1995).
Peterson et al., "Expanding the scope of crystal form evaluation in pharmaceutical science", *J. Pharm. Pharmaceut. Sci.*, 9(3): 317-26 (2006).
Phillips et al., "Discovery of N-[2-[5-[Amino(imino)methyl]-2-hydroxyphenoxyl]-3,5-difluoro-6-[3-(4,5-dihydro-1-methyl-1H-imidazol-2-yl)phenoxy]pyridin-4-yl]-N-methylglycine(ZK-807834): A Potent, selective, and orally active inhibitor of the blood coagulation enzyme factor Xa", *J. Med. Chem.*, 41(19):3557-62 (1998).
Pomorski, "Syntheses of acids, derivatives of 4-hydroxy-1,5-naphthyridine", *Roczniki Chemii, Ann. Soc. Chim. Polonorum*, 48:321-325 (1974).
Potenza et al., "A rapid quantitative bioassay for evaluating the effects of ligands upon receptors that modulate cAMP levels in a melanophore cell line", *Pigment Cell Res.*, 5(6):372-8 (1992).
Prasad et al., "Convenient methods for the reduction of amides, nitriles, carboxylic esters, acids and hydroboration of alkenes using $NaBH_4/I_2$System", *Tetrahedron*, 48(22):4623-8 (1992).
Press et al., "Synthesis and SAR of 6-Substituted purine derivatives as novel selective positive inotropes", *J. Med. Chem.*, 35(24):4509-15 (1992).

Quintela et al., "6-dimethylamino 1H-pyrazolo[3,4-d]pyrimidine derivatives as new inhibitors of inflammatory mediators in intact cells", *Bioorganic & Medicinal Chemistry*, 11:863-8 (2003).
Quintela et al., "Pyrazolopyrimidines: synthesis, effect on histamine release from rat peritoneal mast cells and cytotoxic activity", *Eur. J. Med. Chem.*, 36:321-32 (2001).
Raffel et al., "Diabetes mellitus", Principles and practice of medical Genetics, $3^{rd}$ Ed. 1:1401-40 (1996).
Ram et al., "Chemotherapeutic agents. Part XXII—Synthesis of π-deficient pyrimidines as leishmanicides", *Indian Journal of Chemistry, Section B*, 30B(10):962-5 (1991).
Reed et al., "In-vivo and in-vitro models of type 2 diabetes in pharmaceutical drug discovery", *Diabetes Obes. Metab.*, 1(2):75-86 (1999).
Rehwald et al., "Syntheses of thieno[2,3-d]pyrimidines and aminopyrimidines from 2-alkoxy-5-cyano-4-thioxopyrimidine intermediates", *Heterocycles*, 48(6):1157-67 (1998).
Remington's Pharmaceutical Sciences, $17^{th}$ Ed., (1985), Mack Publishing Company, Easton, PA, p. 1418-19.
Remington's Pharmaceutical Sciences, $16^{th}$ Ed., Mack publishing company, PA., 1980.
Rewcastle et al., "Tyrosine kinase inhibitors. 10. Isomeric 4-[(3-Bromophenyl)amino]pyrido[d]pyrimidines are Potent ATP binding site inhibitors of the tyrosine kinase function of the epidermal growth factor receptor", *J. Med. Chem.*, 39:1823-35 (1996).
Roberts et al., "Peroxy-acid oxidation of NN-disubstituted aminotetrafluoro-, amino-3-chlorotrifluoro-, and amino-3,5-dichlorodifluoro-pyridines", *Journal of the Chemical Society [Section] C: Organic*, 11:1485-91 (1969).
Roberts et al., "Polychloroaromatic compounds. Part I. Oxidation of pentachloropyridine and its NN-disubstituted amino derivatives with peroxyacids", *Journal of the Chemical Society [Section] C: Organic*: 1537-41 (1968).
Robev et al., "4-cyclopropylamino- and 4-cyclobutylamino derivatives of some aryl-substituted 5-cyanopyrimidines", *Diklady Bolgarskoi Akademii Nauk*, 34(12):1677-80 (1981).
Robins et al., "Potential purine antagonists. IV. Synthesis of some 9-methyl-6-substituted-purines$^1$", 79:490-4 (1957).
Roche, Bioreversible Carriers in Drug Design, ed., American Pharmaceutical Association and Pergamon Press (1987).
Rotwein et al., "Polymorphism in the 5' flanking region of the human insulin gene: a genetic marker for non-insulin-dependent diabetes", *N. Engl. J. Med.*, 308(2):65-71 (1983).
Showell et al., "Tetrahydropyridyloxadiazoles: semirigid muscarinic ligands", *J. Med. Chem.*, 34(3):1086-94 (1991).
Šilhár et al., "Facile and efficient synthesis of 6-(hydroxymethyl)purines", *Org. Lett.*, 6(19):3225-8 (2004).
Silvestri et al., "Novel indolyl aryl sulfones active against HIV-1 carrying NNRTI resistance mutations: synthesis and SAR studies", *J. Med. Chem.*, 46(12):2482-93 (2003).
Smith et al., "Effects of positive allosteric modulators of the $GABA_B$ receptor on cocaine self-administration in rats", *Psychopharmacology*, 173(1-2):105-11 (2004).
Soga et al., "Lysophosphatidylcholine enhances glucose-dependent insulin secretion via an orphan G-protein-coupled receptor," *Biochem Biophys Res Commun* (2005) 326:744-751.
Steensma et al., "A novel method for the synthesis of aryl sulfones", *Tetrahedron Ltrs.*, 42:2281-3 (2001).
Sternfeld et al., "Synthesis and serotonergic activity of 3-[2-(pyrrolidin-1-yl)ethyl]indoles: potent agonists for the $h5-HT_{1D}$ receptor with high selectivity over the $h5-HT_{1B}$ receptor", *J. Med. Chem.*, 42(4):677-90 (1999).
Strupczewski et al., "Synthesis and neuroleptic activity of 3-(1-substituted-4-piperidinyl)-1,2-benzisoxazoles", *J. Med. Chem.*, 28(6):761-9 (1985).
Suami et al., "Nucleoside analogs. I. Synthesis of 1,3-dihydroxy-2-(6-substituted-9-purinyl)cyclohexane", *Journal of Heterocyclic Chemistry*, 6(5):663-5 (1969).
Sugimoto et al., "Lithiation of 1H-Pyrazolo[3,4-d]pyrimidine derivative using lithium alkanetellurolate", *Tetrahedron Letters*, 40:2139-40 (1999).
Sugimoto et al., "Preparation of nitrogen-containing π-deficient heteroaromatic Grignard reagents: oxidative magnesiation of nitrogen-containing π-deficient halogenoheteroaromatics using active magnesium", *J. Org. Chem.*, 68:2054-7 (2003).

Terashima et al., "Inhibition of human $O^6$-alkylguanine-DNA alkyltransferase and potentiation of the cytotoxicity of chloroethylnitrosourea by 4(6)-(benzyloxy)-2,6(4)-diamino-5-(nitro or nitroso)pyrimidine derivatives and analogues", *J. Med. Chem.*, 41(4):503-8 (1998).

Thompson et al., "$N^6$,9-disubstituted adenines: potent, selective antagonists at the $A_1$ adenosine receptor", *J. Med. Chem.*, 34:2877-82 (1991).

Thompson et al., "Synthesis and evaluation of 6-(dibromomethyl)-5-nitropyrimidines as potential antitumor agents", *J. Med. Chem.*, 40(5):766-70 (1997).

Turck et al., "Advances in the directed metallation of azines and diazines (pyridines, pyrimidines, pyrazines, pyridazines, quinolines, benzodiazines and carbolines". Part 2: metallation of pyrimidines, pyrazines, pyridazines and benzodiazines, *Tetrahedron*, 57(21):4489-505 (2001).

Ulrich, J., "Crystallization", *Kirk-Othmer Encyclopedia of the Chemical Technology*, Chapter 4, vol. 8, pp. 95-147, (2002).

Urgaonkar et al., "Pd/P(i-BuNCH$_2$CH$_2$)$_3$N: an efficient catalyst for Suzuki cross-coupling of aryl bromides and chlorides with arylboronic acids", *Tetrahedron Letters*, 43(49):8921-4 (2002).

Urwyler et al., "N,N'-dicyclopentyl-2-methylsulfanyl-5-nitro-pyrimidine-4,6-diamine (GS39783) and structurally related compounds: novel allosteric enhancers of γ-aminobutyric acid$_B$ receptor function", *Journal of Pharmacology and Experimental Therapeutics*, 307(1):322-30 (2003).

Vaughan et al., "The reformatsky reaction. I. Zinc and ethyl α-bromoisobutyrate", Dept. of Chem., The Univ. of Michigan, Ann Arbor, MI, 30:1790-5 (1964).

Vice et al., "Concise formation of 4-benzyl piperidines and related derivatives using a Suzuki protocol", *J. Org. Chem.*, 66:2487-92 (2001).

Vice et al., "Concise formation of 4-benzyl piperidines and related derivatives using a Suzuki protocol", *J. Org. Chem.*, 66:2487-92, Supporting Information, pp. S1-S32 (2001).

Vippagunta et al., "Crystalline solids", *Advanced Drug Delivery Reviews*, 48:3-26, 2001.

Wang et al., "Improving the oral efficiency of CNS drug candidates: discovery of highly orally efficacious piperidinyl piperidine M2 muscarinic receptor antagonists", *J. Med. Chem.*, 45(25):5415-18 (2002).

Wells et al., "Regioselective nucleophilic substitutions of fluorobenzene derivatives", *Tetrahedron Letters*, 37(36):6439-42 (1996).

Werbel et al., "Synthesis and antimalarial effects of 5,6-dichloro-2-[(4-[[[4-(diethylamino)1-methylbutyl]amino[[-6-methyl-2-pyrimidinyl)amino]benzimidazole and related benzimidazoles and 1H-Imidazo[4,5-b]pyridines", *J. Het. Chem.*, 10:363-82 (1973).

West, Anthony R., "Solid State Chemistry and its Applications", Wiley, New York, 1988:358 & 365.

Wilson et al., "Microwave-assisted synthesis of 2-aminoquinolines", *Tetrahedron Letters*, 43(4):581-3 (2002).

Wolfe et al., "Scope and limitations of the Pd/BINAP-catalyzed amination of aryl bromides", *J. Org. Chem.*, 65(4):1144-57 (2000).

Wolfe et al., "Simple, efficient catalyst system for the palladium-catalyzed amination of aryl chlorides, bromides, and triflates", *J. Org. Chem.*, 65(4):1158-74 (2000).

Wolter et al., "Copper-catalyzed coupling of aryl iodides with aliphatic alcohols", *Organic Letters*, 4(6):973-6 (2002).

Wolter et al., "Copper-catalyzed coupling of aryl iodides with aliphatic alcohols", *Organic Letters*, 4(6):973-6 (2002), Supporting Information pp. S1-S16.

Wu et al., "One-pot two-step microwave-assisted reaction in constructing 4,5-disubstituted pyrazolopyrimidines", *Org. Lett.*, 5(20):3587-90 (2003).

Yarovenko et al., "New method for the preparation of 5-amino-1,2,4-oxadiazoles", *Bull. Acad. Sci., USSR Div Chem Sci*, 40:1924 (1991).

Yoon et al., "Reaction of diisobutylaluminum hydride with selected organic compounds containing representative functional groups", *J. Org. Chem.*, 50:2443-50 (1985).

Zamponi et al., "Unique structure-activity relationship for 4-isoxazolyl-1,4-dihydropyridines", *J. Med. Chem.*, 46:87-96 (2003).

Zamponi et al., "Unique structure-activity relationship for 4-isoxazolyl-1,4-dihydropyridines", *J. Med. Chem.*, Supporting Information pp. 1-31 (2003).

Zhang et al., "Preparation of 1-(Tri-n-butylstannyl) Furanoid Glycals and their use in palladium-mediated coupling reactions", *Tetrahedron Letters*, 34(10):1571-4 (1993).

Zhu et al., "Synthesis and mode of action of $^{125}$I- and $^3$H-labeled thieno[2,3-c]pyridine antagonists of cell adhesion molecule expression", *J. Org. Chem.*, 67(3):943-8 (2002).

International Search Report for PCT/US2006/000565, dated May 22, 2006.

* cited by examiner

PROCESSES FOR PREPARING AROMATIC ETHERS

CROSS REFERENCE TO RELATED APPLICATIONS

This application claims the benefit of U.S. Ser. No. 60/642,627, filed Jan. 10, 2005, the disclosure of which is incorporated herein by reference in its entirety.

FIELD OF THE INVENTION

The present invention relates to processes for preparing aromatic ether compounds that are modulators of glucose metabolism and therefore useful in the treatment of metabolic disorders such as diabetes and obesity.

BACKGROUND OF THE INVENTION

Modulation of G-protein coupled receptors has been well-studied for controlling various metabolic disorders. Small molecule modulators of the receptor RUP3, a G-protein coupled-receptor described in, for example, GenBank (see, e.g., accession numbers XM_066873 and AY288416), have been shown to be useful for treating or preventing certain metabolic disorders. In particular, aromatic ethers and similar compounds, which are described in U.S. Ser. No. 10/888,747, are shown to be effective modulators of the RUP3 receptor and are useful in the treatment of various metabolic-related disorders such as type I diabetes, type II diabetes, inadequate glucose tolerance, insulin resistance, hyperglycemia, hyperlipidemia, hypertriglyceridemia, hypercholesterolemia, dyslipidemia or syndrome X. The aromatic ethers are also useful in controlling weight gain, controlling food intake, and inducing satiety in mammals. The promising nature of these RUP3 modulators in treating or preventing a number of common diseases evidences a need for more efficient processes of making these compounds. The processes described herein are directed toward this and other current needs.

SUMMARY OF THE INVENTION

The present invention provides processes for preparing compounds of Formula I:

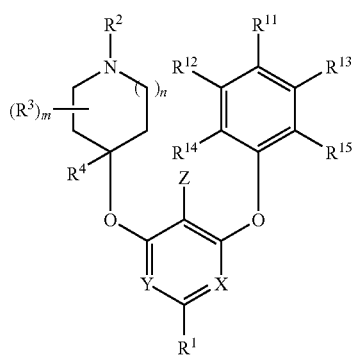

wherein constituent members are defined herein, comprising reacting a compound of Formula II:

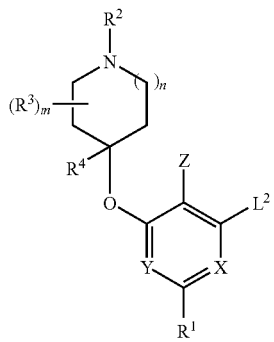

with compound of Formula III:

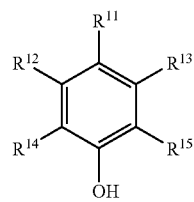

in the presence of a base, thereby forming the compound of Formula I.

The present invention also provides processes for preparing compounds of Formula II by:
a) combining a compound of Formula IV:

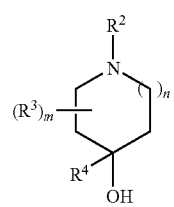

with a compound of Formula V:

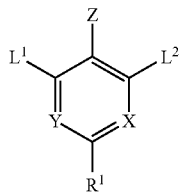

to form a mixture; and
b) adding a base to the mixture, thereby forming the compound of Formula II.

The present invention further provides bulk samples of the compound of Formula I or II prepared according to the processes herein.

DETAILED DESCRIPTION

The present invention is directed to processes and intermediates for the preparation of aromatic ethers that are useful as RUP3 modulators for the treatment of metabolic disorders such as diabetes and obesity.

Example processes and intermediates of the present invention are provided below in Scheme I, wherein constituent members of the formulae depicted therein are defined below.

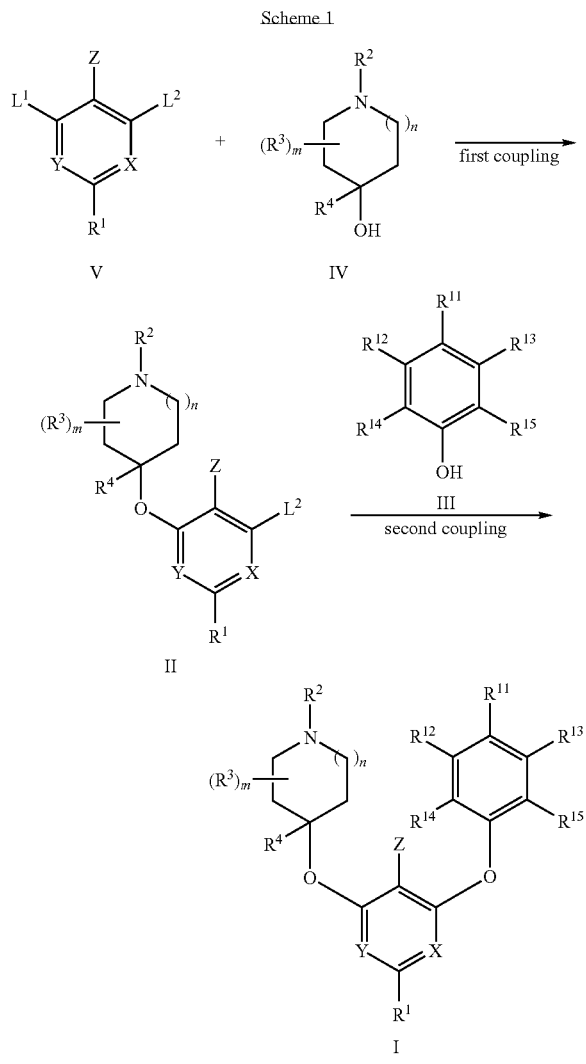

Scheme 1

The present invention provides processes, such as exemplified in Scheme I, involving compounds of Formulas I, II, III, IV, and V, or salt forms thereof, wherein:

$L^1$ is a leaving group;
$L^2$ is a leaving group;
X is N or $CR^7$;
Y is N or $CR^8$;
Z is $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, $C_{1-2}$ alkylamino, $C_{2-4}$ dialkylamino, carbamimidoyl, carbo-$C_{1-6}$-alkoxy, carboxamide, carboxy, cyano, $C_{3-7}$ cycloalkyl, $C_{4-8}$ diacylamino, $C_{2-6}$ dialkylcarboxamide, $C_{2-4}$ dialkylthiocarboxamide, $C_{2-6}$ dialkylsulfonamide, $C_{2-6}$ dialkylsulfonylamino, formyl, $C_{1-4}$ haloalkoxy, $C_{1-4}$ haloalkyl, $C_{1-4}$ haloalkylcarboxamide, $C_{1-4}$ haloalkylsulfinyl, $C_{1-4}$ haloalkylsulfonyl, $C_{1-4}$ haloalkylthio, halogen, aryl, heteroaryl, heterocycloalkyl, hydroxyl, hydroxycarbamimidoyl, hydroxylamino, nitro, or tetrazolyl; wherein said $C_{1-8}$ alkyl, $C_{3-7}$ cycloalkyl, and heterocycloalkyl are each optionally substituted with 1, 2, 3 or 4 groups selected from $C_{1-5}$ acyl, $C_{1-5}$ acyloxy, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-2}$ alkylamino, $C_{2-4}$ dialkylamino, carbo-$C_{1-6}$-alkoxy, carboxamide, carboxy, cyano, formyl, $C_{1-4}$ haloalkoxy, $C_{1-4}$ haloalkylsulfinyl, $C_{1-4}$ haloalkylsulfonyl, $C_{1-4}$ haloalkylthio, halogen, hydroxyl, hydroxylamino, and nitro;

$R^1$ is H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-7}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, or hydroxyl;

$R^2$ is $-R^{22}$, $-CR^{23}R^{24}C(O)-R^{22}$, $-C(O)CR^{23}R^{24}-R^{22}$, $-C(O)-R^{22}$, $-CR^{23}R^{24}C(O)NR^{25}-R^{22}$, $-NR^{25}C(O)CR^{23}R^{24}-R^{22}$, $-C(O)NR^{23}-R^{22}$, $-NR^{23}C(O)-R^{22}$, $-C(O)O-R^{22}$, $-OC(O)-R^{22}$, $-C(S)-R^{22}$, $-C(S)NR^{23}-R^{22}$, $-NR^{23}C(S)-R^{22}$, $-C(S)O-R^{22}$, $-OC(S)-R^{22}$, $-CR^{23}R^{24}-R^{22}$, or $-S(O)_2-R^{22}$;

$R^3$ is $C_{1-3}$ alkyl, $C_{1-4}$ alkoxy, carboxy, cyano, $C_{1-3}$ haloalkyl, or halogen;

$R^4$ is H, $C_{1-8}$ alkyl or $C_{3-7}$ cycloalkyl, wherein said $C_{1-8}$ alkyl is optionally substituted with $C_{1-4}$ alkoxy, $C_{3-7}$ cycloalkyl, or heteroaryl;

$R_7$ and $R_8$ are each, independently, H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-7}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, or hydroxyl;

$R^{11}$ is $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, arylsulfonyl, carbamimidoyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, $C_{2-6}$ dialkylthiocarboxamide, guanidinyl, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocycloalkyl, heterocycloalkyl-oxy, heterocycloalkylsulfonyl, heterocycloalkyl-carbonyl, heteroaryl, heteroarylcarbonyl, hydroxyl, nitro, $C_{4-7}$ oxo-cycloalkyl, phenoxy, phenyl, sulfonamide, sulfonic acid, or thiol; and wherein said $C_{1-5}$ acyl, $C_{1-6}$ acylsulfonamide, $C_{1-4}$ alkoxy, $C_{1-8}$ alkyl, $C_{1-4}$ alkylamino, $C_{1-6}$ alkylsulfonamide, $C_{1-4}$ alkylsulfonyl, $C_{1-4}$ alkylthio, arylsulfonyl, carbamimidoyl, $C_{2-6}$ dialkylamino, heterocycloalkyl, heterocycloalkyl-carbonyl, heteroaryl, phenoxy and phenyl are each optionally substituted with 1 to 5 substituents selected independently from $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro, phenyl, and phosphonooxy, wherein said $C_{1-7}$ alkyl and $C_{1-4}$ alkylcarboxamide are each optionally substituted with 1 to 5 substituents selected from $C_{1-4}$ alkoxy and hydroxy;

$R^{12}$, $R^{13}$, $R^{14}$, and $R^{15}$ are each, independently, H, $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, or nitro;

$R^{22}$ is H, $C_{1-8}$ alkyl, $C_{3-7}$ cycloalkyl, phenyl, heteroaryl, or heterocyclic each optionally substituted with 1 to 5 substituents selected from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, heterocyclic, hydroxyl, hydroxylamino, nitro, phenyl, phenoxy, and sulfonic acid, wherein said $C_{1-7}$ alkyl, heteroaryl, phenyl and phenoxy are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino, and nitro;

$R^{23}$, $R^{24}$ and $R^{25}$ are each, independently, H or $C_{1-8}$ alkyl;

n is 0 or 1; and m is 0, 1, 2, 3, or 4.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables (e.g., n, m, $R_1$, $R_2$, $R_3$, $R_4$, $R_{11}$, $R_{12}$, $R_{13}$, $R_{14}$, $R_{15}$, X, Y, Z, etc.) contained within the generic chemical formulae described herein [e.g. I, II, III, etc.] and process steps disclosed herein are specifically embraced by the present invention just as if they were explicitly disclosed, to the extent that such combinations embrace compounds that result in stable compounds (ie., compounds that can be isolated, characterized and tested for biological activity). In addition, all subcombinations of the chemical groups listed in the embodiments describing such variables, as well as all subcombinations of process steps, are also specifically embraced by the present invention just as if each of such subcombination of chemical groups and process steps were explicitly disclosed herein.

In some embodiments, $L^1$ is halo.

In some embodiments, $L^1$ is Cl.

In some embodiments, $L^2$ is halo.

In some embodiments, $L^2$ is Cl.

In some embodiments, X is N.

In some embodiments, Y is N.

In some embodiments, both X and Y are N.

In some embodiments, Z is $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, $C_{1-2}$ alkylamino, $C_{2-4}$ dialkylamino, carbamimidoyl, carbo-$C_{1-6}$-alkoxy, carboxamide, carboxy, cyano, $C_{3-7}$ cycloalkyl, $C_{4-8}$ diacylamino, $C_{2-6}$ dialkylcarboxamide, $C_{2-6}$ dialkylthiocarboxamide, $C_{2-6}$ dialkylsulfonamide, $C_{2-6}$ dialkylsulfonylamino, formyl, $C_{1-4}$ haloalkoxy, $C_{1-4}$ haloalkyl, $C_{1-4}$ haloalkylcarboxamide, $C_{1-4}$ haloalkylsulfinyl, $C_{1-4}$ haloalkylsulfonyl, $C_{1-4}$ haloalkylthio, halogen, aryl, heteroaryl, heterocycloalkyl, hydroxyl, hydroxycarbamimidoyl, hydroxylamino, nitro, or tetrazolyl.

In some embodiments, Z is $C_{1-5}$ acyl, $C_{1-5}$ acyloxy, $C_{2-6}$ alkenyl, $C_{1-4}$ alkoxy, $C_{1-8}$ alkyl, $C_{2-6}$ alkynyl, formyl, $C_{1-4}$ haloalkoxy, $C_{1-4}$ haloalkyl, halogen, hydroxyl, or nitro.

In some embodiments, Z is $C_{1-8}$ alkyl.

In some embodiments, Z is methyl, ethyl or propyl.

In some embodiments, Z is methyl.

In some embodiments, $R^1$ is H.

In some embodiments, $R^2$ is —C(O)O—$R^{22}$.

In some embodiments, $R^2$ is —C(O)O—$R^{22}$ and $R^{22}$ is $C_{1-8}$ alkyl or $C_{3-7}$ cycloalkyl.

In some embodiments, $R^2$ is —C(O)O—$R^{22}$ and $R^{22}$ is $C_{1-4}$ alkyl.

In some embodiments, $R^2$ is —C(O)O—$R^{22}$ and $R^{22}$ is methyl, ethyl, or prop-1-yl, prop-2-yl.

In some embodiments, $R^2$ is —C(O)O—$R^{22}$ and $R^{22}$ is prop-2-yl.

In some embodiments, $R^4$ is H.

In some embodiments, n is 1.

In some embodiments, m is 0.

In some embodiments, $R^{11}$ is $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, arylsulfonyl, carbamimidoyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, $C_{2-6}$ dialkylthiocarboxamide, guanidinyl, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocycloalkyl-oxy, heterocycloalkylsulfonyl, heterocycloalkylcarbonyl, heteroaryl, heteroarylcarbonyl, hydroxyl, nitro, $C_{4-7}$ oxo-cycloalkyl, phenoxy, phenyl, sulfonamide, sulfonic acid, or thiol.

In some embodiments, $R^{11}$ is $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, or $C_{1-4}$ alkylsulfonyl.

In some embodiments, $R^{11}$ is $C_{1-4}$ alkylsulfinyl or $C_{1-4}$ alkylsulfonyl.

In some embodiments, $R^{11}$ is $C_{1-4}$ alkylsulfonyl.

In some embodiments, $R^{11}$ is methylsulfonyl or ethylsulfonyl.

In some embodiments, $R^{11}$ is methylsulfonyl.

In some embodiments, $R^{12}$, $R^{13}$, $R^{14}$, and $R^{15}$ are each, independently, H, $C_{2-6}$ alkenyl, $C_{1-4}$ alkoxy, $C_{1-8}$ alkyl, $C_{2-6}$ alkynyl, cyano, halogen, $C_{1-4}$ haloalkoxy, $C_{1-4}$ haloalkyl, hydroxyl, or nitro.

In some embodiments, $R^{12}$, $R^{13}$, $R^{14}$, and $R^{15}$ are each, independently, H, $C_{1-4}$ alkoxy, $C_{1-8}$ alkyl, cyano, halogen, hydroxyl, or nitro.

In some embodiments, $R^{12}$, $R^{13}$, $R^{14}$, and $R^{15}$ are each, independently, H or halogen.

In some embodiments, $R^{15}$ is other than H.

In some embodiments, $R^{15}$ is halogen.

In some embodiments, $R^{15}$ is F.

In some embodiments, $R^{12}$, $R^{13}$, and $R^{14}$ are each H and $R^{15}$ is other than H.

In some embodiments, $R^{11}$ is $C_{1-4}$ alkylsulfonyl; $R^{12}$, $R^{13}$, and $R^{14}$ are each H; and $R^{15}$ is halogen.

In some embodiments:
X is N;
Y is N;
Z is $C_{1-5}$ acyl, $C_{1-5}$ acyloxy, $C_{2-6}$ alkenyl, $C_{1-4}$ alkoxy, $C_{1-8}$ alkyl, $C_{2-6}$ alkynyl, formyl, $C_{1-4}$ haloalkoxy, $C_{1-4}$ haloalkyl, halogen, hydroxyl, or nitro;
$R^1$ is H;
$R^2$ is —C(O)O—$R^{22}$;
$R^4$ is H;
$R^{11}$ is $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, or $C_{1-4}$ alkylsulfonyl;
$R^{12}$, $R^{13}$, $R^{14}$, and $R^{15}$ are each, independently, H, $C_{2-6}$ alkenyl, $C_{1-4}$ alkoxy, $C_{1-8}$ alkyl, $C_{2-6}$ alkynyl, cyano, halogen, $C_{1-4}$ haloalkoxy, $C_{1-4}$ haloalkyl, hydroxyl, or nitro;
n is 1; and
m is 0 or 1.

In some embodiments:
X is N;
Y is N;
Z is $C_{1-8}$ alkyl;
$R^1$ is H;
$R^2$ is —C(O)O—$R^{22}$;
$R^4$ is H;
$R^{11}$ is $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, or $C_{1-4}$ alkylsulfonyl;
$R^{12}$, $R^{13}$, and $R^{14}$ are each H;
$R^{15}$ is $C_{2-6}$ alkenyl, $C_{1-4}$ alkoxy, $C_{1-8}$ alkyl, $C_{2-6}$ alkynyl, cyano, halogen, $C_{1-4}$ haloalkoxy, $C_{1-4}$ haloalkyl, hydroxyl, or nitro;
n is 1; and
m is 0 or 1.

In some embodiments:
X is N;
Y is N;
Z is $C_{1-8}$ alkyl;
$R^1$ is H;
$R^2$ is —C(O)O—$R^{22}$;
$R^4$ is H;
$R^{11}$ is $C_{1-4}$ alkylsulfinyl or $C_{1-4}$ alkylsulfonyl;
$R^{12}$, $R^{13}$, and $R^{14}$ are each H;
$R^{15}$ is $C_{2-6}$ alkenyl, $C_{1-4}$ alkoxy, $C_{1-8}$ alkyl, $C_{2-6}$ alkynyl, cyano, halogen, $C_{1-4}$ haloalkoxy, $C_{1-4}$ haloalkyl, hydroxyl, or nitro;
$R^{22}$ is $C_{1-4}$ alkyl;
n is 1; and
m is 0.

In some embodiments:
X is N;
Y is N;
Z is methyl;
$R^1$ is H;
$R^2$ is —C(O)O—$R^{22}$;
$R^4$ is H;
$R^{11}$ is methylsulfonyl;
$R^{12}$, $R^{13}$, and $R^{14}$ are each H;
$R^{15}$ is F;
$R^{22}$ is prop-2-yl;
n is 1; and
m is 0.

In some embodiments, the present invention provides a process for preparing a compound of Formula I:

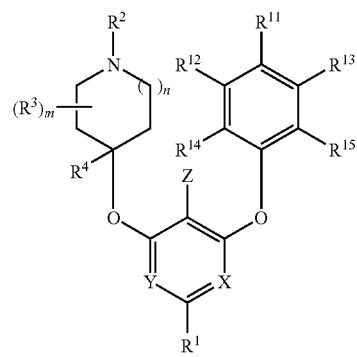

by reacting a compound of Formula II:

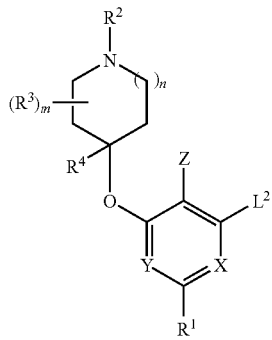

with compound of Formula III:

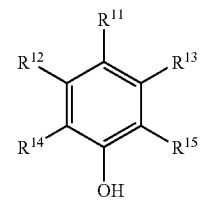

in the presence of a base, thereby forming the compound of Formula I.

The reacting of II with III can be further carried out in the presence of a salt, such as a tetrasubstituted ammonium salt or an iodide salt. A tetrasubstituted ammonium salt includes a salt of formula $[N(R)_4][X^1]$; where $X^1$ is any monoanion such as fluoride, chloride, bromide, iodide, and the like, and each R is, independently, $C_{1-8}$ alkyl, aryl, arylalkyl, cycloalkyl, cycloalkylalkyl, heteroaryl, heteroarylalkyl, heterocyclic, or heterocyclic alkyl, each of which can be optionally substituted by halo, $C_{1-4}$ alkyl, $C_{1-4}$ haloalkyl, $C_{1-4}$ alkoxy, or $C_{1-4}$ haloalkoxy. In some embodiments, the tetrasubstituted ammonium salt is a tetra($C_{1-8}$ alkyl)ammonium salt. In further embodiments, the tetrasubstituted ammonium salt is a tetrabutylammonium salt. In further embodiments, the tetrasubstituted ammonium salt is a halide salt. In further embodiments, the tetrasubstituted ammonium salt is an iodide salt. In further embodiments, the tetrasubstituted ammonium salt is tetrabutylammonium iodide. In further embodiments, the tetrasubstituted ammonium salt is a fluorine salt. In further embodiments, the tetrasubstituted ammonium salt is tetrabutylammonium fluoride $[(CH_3CH_2CH_2CH_2)_4NF]$.

The reacting of II with III can be further carried out in the presence of a salt, such as an alkali metal halide salt. Alkali metal halide salts are known in the art and include salts of formula M-Halide, wherein M is an alkali metal and halide is F, Cl, Br, and I. Examples of an alkali metal halide salt include, for example, NaF, NaCl, NaBr, NaI, KF, KCl, KBr, KI, CsF, CsCl, CsBr, CsI, and the like.

In the reacting of II with III, the base can be any that is routinely used in the art for similar coupling reactions. In some embodiments, the base is an alkali metal amide, alkali metal hydride, alkali metal carbonate, or an alkali metal hydrogencarbonate. In further embodiments, the base is an alkali metal carbonate. In yet a further embodiment, the base is $K_2CO_3$.

In some embodiments, the reacting of II with III can be carried out at elevated temperature. For example, the reaction mixture can be heated to a temperature of about 100 to about 150, about 120 to about 140, or about 130 to about 135° C.

In some embodiments, the reacting of II with III is carried out in a solvent. Suitable solvents include, for example polar solvents or solvents having a boiling point above about 100° C. Example polar solvents include dimethylsulfoxide (DMSO), dimethylformamide (DMF), dimethylacetate (DMA), N-methylpyrrolidine (NMP), acetonitrile, propionitrile, and the like. Example high boiling solvents include DMSO, DMF, DMA, and the like. In some embodiments, the solvent includes DMSO.

In some embodiments, the reacting of II and III is carried out where the molar ratio of the compound of Formula II to Formula III is about 1:1. In some embodiments, the compound of Formula II is provided in slight molar excess relative to the amount of compound of Formula III. In further embodiments, the molar ratio of base to amount of compound of Formula III is about 2:1 to about 1:1, about 1.3:1 to about 1.1:1, or about 1.2:1. In yet further embodiments, the molar ratio of tetrasubstituted ammonium salt to amount of compound of Formula III is about 1:1 to about 0.1:1, about 0.8:1 to about 0.5:1, or about 0.7:1 to about 0.6:1.

The compound Formula II can be prepared by:
a) combining a compound of Formula IV:

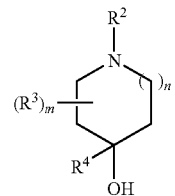

IV with a compound of Formula V:

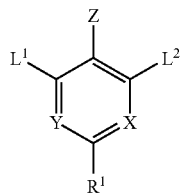

V to form a mixture; and
b) adding a base to the mixture, thereby forming the compound of Formula II.

The base which is added to the mixture of IV and V can be any suitable base including, for example, $C_{1-6}$ alkoxide salts, alkali metal amides, alkali metal hydrides, alkali metal carbonates, or alkali metal hydrogencarbonates. In some embodiments, the base is a $C_{1-6}$ alkoxide salt such as an alkali salt of t-butoxide. In some embodiments, the base is potassium t-butoxide. Base can be optionally added in one or more portions such as, for example, two portions.

In some embodiments, the combining of IV and V as well as the adding step are carried out in a solvent. Example suitable solvents include ether solvents such as dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, or t-butyl methyl ether. In some embodiments, the solvent includes tetrahydrofuran. Other suitable solvents include DMF, DMA, NMP, DMSO, acetonitrile and propionitrile.

The adding of base can be optionally carried out at reduced temperature. For example, the addition can be carried out at a temperature below about 25, below about 15, below about 10, below about 5, or below about 0° C.

In some embodiments, the molar ratio of compound IV to compound V is about 1:1. In further embodiments, the molar ratio of compound IV to compound V to base is about 1:1:1. In some embodiments, the molar ratio of base to compound V is about 1.02:1 to about 0.90:1 or about 1:1 to about 0.96:1.

The compounds of Formulas III, IV, and V can be prepared according to routine methods in the art. Example preparations of these compounds are provided such in U.S. application Ser. No. 10/888,747, which is incorporated herein by reference in its entirety.

While routine isolation and purification procedures can yield substantially pure preparations (e.g., bulk samples) of the compound of Formula I, impurities which are characteristic of the procedures described herein can occasionally persist. For example, in the preparation of compounds of Formula II, compounds of Formula IIa can optionally be present as byproducts which optionally can be carried over to the preparation of Formula I if the byproduct is present in starting material II.

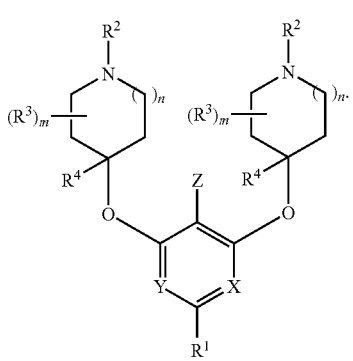

IIa

In some embodiments, bulk samples of Formula II made by the processes described herein can contain a detectable amount of compound of Formula IIa. The amount of compound of Formula IIa in preparations of Formula II can be, for example, less than about 5%, less than about 3%, less than about 2%, less than about 1%, less than about 0.5%, less than about 0.2%, less than about 0.1%, less than about 0.05%, less than about 0.02%, or less than about 0.01% by weight.

In some embodiments, bulk samples of Formula I made by the processes described herein can contain a detectable amount of compound of Formula IIa. The amount of compound of Formula IIa in preparations of Formula I can be, for example, less than about 5%, less than about 3%, less than about 2%, less than about 1%, less than about 0.5%, less than about 0.2%, less than about 0.1%, less than about 0.05%, less than about 0.02%, or less than about 0.01% by weight.

In some embodiments, the byproduct is compound of Formula IIb:

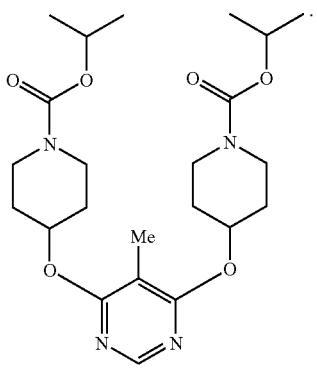

IIb

The compound of Formula IIa and other byproducts can be detected and quantified by routine methods including, for example, proton nuclear magnetic resonance, high performance liquid chromatography, mass spectrometry, and the like. The amount of compound of Formula IIa and other byproducts in bulk samples prepared according to the processes herein can be reduced or substantially eliminated by routine methods such as recrystallization or chromatography techniques.

The term "bulk sample" is used herein consistently with its meaning in the art which, for example, refers to an amount of product prepared according to a given process or procedure. Bulk samples can be any size, but typically range from 1 mg on upward to several thousands of kilograms or more.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

The term "$C_{i-j}$" denotes the number of carbon atoms in the moiety to which the term refers. For example, $C_{1-8}$ alkyl (where i is 1 and j is 8) refers to an alkyl group having 1 ($C_1$), 2 ($C_2$), 3 ($C_3$), 4 ($C_4$), 5 ($C_5$), 6 ($C_6$), 7 ($C_7$), or 8 ($C_8$) carbon atoms.

The term "acyl" denotes a carbonyl (C=O) substituted by an alkyl radical, wherein the definition of alkyl has the same definition as described herein. Some examples include, but are not limited to, acetyl, propionyl, n-butanoyl, iso-butanoyl, sec-butanoyl, t-butanoyl (i.e., pivaloyl), pentanoyl and the like.

The term "acyloxy" denotes —O— substituted by an acyl radical, wherein acyl has the same definition has described herein. Some examples include but are not limited to acetyloxy, propionyloxy, butanoyloxy, iso-butanoyloxy, sec-butanoyloxy, t-butanoyloxy and the like.

The term "acylsulfonamide" refers to a sulfonamide substituted by acyl on the sulfonamide N-atom, wherein the definitions for acyl and sulfonamide have the same meaning as described herein, and an acylsulfonamide can be represented by the following formula:

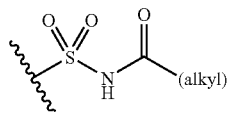

Some embodiments of the present invention include $C_{1-5}$ acylsulfonamide, $C_{1-4}$ acylsulfonamide, $C_{1-3}$ acylsulfonamide, or $C_{1-2}$ acylsulfonamide. Examples of acylsulfonamides include, but are not limited to, acetylsulfamoyl [—S(=O)$_2$NHC(=O)Me], propionylsulfamoyl [—S(=O)$_2$NHC(=O)Et], isobutyrylsulfamoyl, butyrylsulfamoyl, 2-methyl-butyrylsulfamoyl, 3-methyl-butyrylsulfamoyl, 2,2-dimethyl-propionylsulfamoyl, pentanoylsulfamoyl, 2-methyl-pentanoylsulfamoyl, 3-methyl-pentanoylsulfamoyl, 4-methyl-pentanoylsulfamoyl, and the like.

The term "alkenyl" denotes an alkyl radical containing having at least one carbon-carbon double bond. In some embodiments, the alkenyl group is $C_{2-6}$ alkenyl, $C_{2-5}$ alkenyl, $C_{2-4}$ alkenyl, $C_{2-3}$ alkenyl or $C_2$ alkenyl. Both E and Z isomers are embraced by the term "alkenyl." Furthermore, the term "alkenyl" includes groups with 1, 2, 3, 4 or more double bonds. Accordingly, if more than one double bond is present then the bonds may be all E or Z or a mixtures of E and Z. Examples of an alkenyl include vinyl, allyl, 2-butenyl, 3-butenyl, 2-pentenyl, 3-pentenyl, 4-pentenyl, 2-hexenyl, 3-hexenyl, 4-hexenyl, 5-hexanyl, 2,4-hexadienyl and the like.

The term "alkoxy" as used herein denotes a radical alkyl, as defined herein, attached directly to an oxygen atom.

Examples include methoxy, ethoxy, n-propoxy, iso-propoxy, n-butoxy, t-butoxy, iso-butoxy, sec-butoxy and the like.

The term "alkyl" denotes a straight or branched hydrocarbon radical. In some embodiments, the alkyl group contains 1 to 8 carbons, 1 to 7 carbons, 1 to 6 carbons, 1 to 5 carbons, 1 to 4 carbons, 1 to 3 carbons, 1 or 2 carbons. Examples of alkyl groups include, but are not limited to, methyl, ethyl, n-propyl, iso-propyl, n-butyl, sec-butyl, iso-butyl, t-butyl, pentyl, iso-pentyl, t-pentyl, neo-pentyl, 1-methylbutyl [i.e., —CH(CH$_3$)CH$_2$CH$_2$CH$_3$], 2-methylbutyl [i.e., —CH$_2$CH(CH$_3$)CH$_2$CH$_3$], n-hexyl and the like.

The term "alkylcarboxamido" or "alkylcarboxamide" denotes a single alkyl group attached to the nitrogen or carbon of an amide group, wherein alkyl has the same definition as found herein. The alkylcarboxamide may be represented by the following:

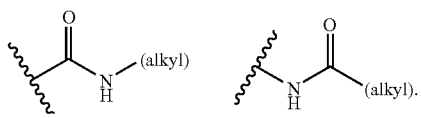

Examples include, but are not limited to, N-methylcarboxamide, N-ethylcarboxamide, N-n-propylcarboxamide, N-iso-propylcarboxamide, N-n-butylcarboxamide, N-sec-butylcarboxamide, N-iso-butylcarboxamide, N-t-butylcarboxamide and the like.

The term "alkylene" refers to a divalent alkyl group. In some embodiments, alkylene refers to, for example, —CH$_2$—, —CH$_2$CH$_2$—, —CH$_2$CH$_2$CH$_2$—, and the like. In some embodiments, alkylene refers to —CH—, —CHCH$_2$—, —CHCH$_2$CH$_2$—, and the like wherein these examples relate generally to "A".

The term "alkylsulfinyl" denotes —S(O)— substituted by alkyl, wherein the alkyl radical has the same definition as described herein. Examples include, but not limited to, methylsulfinyl, ethylsulfinyl, n-propylsulfinyl, iso-propylsulfinyl, n-butylsulfinyl, sec-butylsulfinyl, iso-butylsulfinyl, t-butyl, and the like.

The term "alkylsulfonamide" refers to the groups

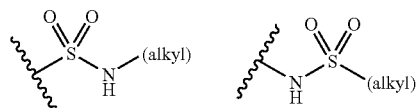

wherein alkyl has the same definition as described herein.

The term "alkylsulfonyl" denotes —S(O)$_2$— substituted by alkyl, wherein the alkyl radical has the same definition as described herein. Examples include, but are not limited to, methylsulfonyl, ethylsulfonyl, n-propylsulfonyl, iso-propyl-sulfonyl, n-butylsulfonyl, sec-butylsulfonyl, iso-butylsulfo-nyl, t-butyl, and the like.

The term "alkylthio" denotes —S— substituted by alkyl, wherein the alkyl radical has the same definition as described herein. Examples include, but not limited to, methylsulfanyl (i.e., CH$_3$S—), ethylsulfanyl, n-propylsulfanyl, iso-propyl-sulfanyl, n-butylsulfanyl, sec-butylsulfanyl, iso-butylsulfa-nyl, t-butyl, and the like.

The term "alkylthiocarboxamide" denotes a thioamide of the following formulae:

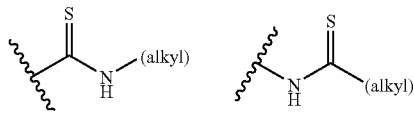

wherein alkyl has the same definition as described herein.

The term "alkylthioureyl" denotes the group of the formula: —NC(S)N— wherein one or both of the nitrogens are substituted with the same or different alkyl groups, and alkyl has the same definition as described herein. Examples of an alkylthioureyl include, but are not limited to, CH$_3$NHC(S)NH—, NH$_2$C(S)NCH$_3$—, (CH$_3$)$_2$N(S)NH—, (CH$_3$)$_2$N(S)NH—, (CH$_3$)$_2$N(S)NCH$_3$—, CH$_3$CH$_2$NHC(S)NH—, CH$_3$CH$_2$NHC(S)NCH$_3$—, and the like.

The term "alkylureyl" denotes the group of the formula: —NC(O)N— wherein one or both of the nitrogens are substituted with the same or different alkyl group, wherein alkyl has the same definition as described herein. Examples of an alkylureyl include, but not limited to, CH$_3$NHC(O)NH—, NH$_2$C(O)NCH$_3$—, (CH$_3$)$_2$N(O)NH—, (CH$_3$)$_2$N(O)NH—, (CH$_3$)$_2$N(O)NCH$_3$—, CH$_3$CH$_2$NHC(O)NH—, CH$_3$CH$_2$NHC(O)NCH$_3$—, and the like.

The term "alkynyl" denotes an alkyl group having at least one carbon-carbon triple bond. In some embodiments, the alkynyl group has 2 to 8 carbons, 2 to 7 carbons, 2 to 6 carbons, 2 to 5 carbons, 2 to 4 carbons, 2 to 3 carbons, or 2 carbons. Examples of alkynyl groups include, but are not limited to, ethynyl, 1-propynyl, 2-propynyl, 1-butynyl, 2-bu-tynyl, 3-butynyl, 1-pentynyl, 2-pentynyl, 3-pentynyl, 4-pen-tynyl, 1-hexynyl, 2-hexynyl, 3-hexynyl, 4-hexynyl, 5-hexy-nyl and the like. Additionally, an alkynyl group can have 1, 2, 3, 4 or more triple bonds, forming for example, di- and tri-ynes.

The term "amino" denotes the group —NH$_2$.

The term "alkylamino" denotes amino substituted by alkyl, wherein the alkyl radical has the same meaning as described herein. Some examples include, but not limited to, methy-lamino, ethylamino, n-propylamino, iso-propylamino, n-bu-tylamino, sec-butylamino, iso-butylamino, t-butylamino, and the like.

The term "aryl" denotes monocyclic or polycyclic aromatic hydrocarbons such as, for example, phenyl, naphthyl, anthracenyl, phenanthrenyl, indanyl, indenyl, and the like. In some embodiments, aryl groups have from 6 to about 20 carbon atoms.

The term "arylalkyl" denotes alkyl substituted with an aryl group. Examples of an "arylalkyl" include benzyl, pheneth-ylene and the like.

The term "arylcarboxamido" denotes an amide group substituted by an aryl group on the N-atom, wherein aryl has the same definition as found herein. An example is N-phenylcar-boxamide.

The term "arylureyl" denotes the group —NC(O)N— where one of the nitrogens are substituted with an aryl.

The term "benzyl" denotes the group —CH$_2$C$_6$H$_5$.

The term "carbamimidoyl" refers to a group of the following chemical formula:

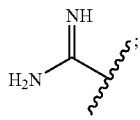

and in some embodiments, one or both hydrogens are replaced with another group. For example, one hydrogen can be replaced with a hydroxyl group to give a N-hydroxycarbamimidoyl group, or one hydrogen can be replaced with an alkyl group to give N-methylcarbamimidoyl, N-ethylcarbamimidoyl, N-propylcarbamimidoyl, N-butylcarbamimidoyl, and the like.

The term "carboalkoxy" refers to an alkyl ester of a carboxylic acid, wherein the alkyl group is as defined herein. Examples include, but not limited to, carbomethoxy, carboethoxy, carbopropoxy, carboisopropoxy, carbobutoxy, carbo-sec-butoxy, carbo-iso-butoxy, carbo-t-butoxy, carbo-n-pentoxy, carbo-iso-pentoxy, carbo-t-pentoxy, carbo-neo-pentoxy, carbo-n-hexyloxy, and the like.

The term "carboxamide" refers to the group —$CONH_2$.

The term "carboxy" or "carboxyl" denotes the group —$CO_2H$; also referred to as a carboxylic acid group.

The term "cyano" denotes the group —CN.

The term "cycloalkenyl" denotes a non-aromatic ring radical containing 3 to 6 ring carbons and at least one double bond; some embodiments contain 3 to 5 carbons; some embodiments contain 3 to 4 carbons. Examples include cyclopropenyl, cyclobutenyl, cyclopentenyl, cyclopentenyl, cyclohexenyl, and the like.

The term "cycloalkyl" denotes a saturated, cyclic hydrocarbon containing, for example, 3 to 14, 1 to 10, 3 to 8, 3 to 7, 3 to 6, 3 to 5, or 3 to 4 carbons. Examples include cyclopropyl, cyclobutyl, cyclopentyl, cyclopenyl, cyclohexyl, cycloheptyl and the like.

The term "cycloalkylalkyl" denotes an alkyl group substituted by a cycloalkyl group.

The term "cycloalkylene" refers to a divalent cycloalkyl radical. In some embodiments, the two bonding groups are on the same carbon, for example:

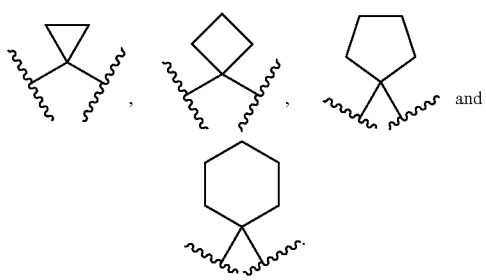

In some embodiments, the two bonding groups are on different carbons.

The term "diacylamino" denotes an amino group substituted with two acyl groups, wherein the acyl groups may be the same or different, such as:

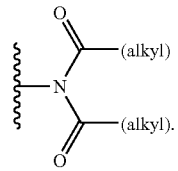

Examples of diacylamino groups include, but limited to, diacetylamino, dipropionylamino, acetylpropionylamino and the like.

The term "dialkylamino" denotes an amino group substituted with two of the same or different alkyl radicals, wherein alkyl has the same definition as described herein. Some examples include, but not limited to, dimethylamino, methylethylamino, diethylamino, methylpropylamino, methylisopropylamino, ethylpropylamino, ethylisopropylamino, dipropylamino, propylisopropylamino and the like.

The term "dialkylcarboxamido" or "dialkylcarboxamide" denotes an amide substituted by two alkyl radicals, that are the same or different. Dialkylcarboxamidos can be represented by the following groups:

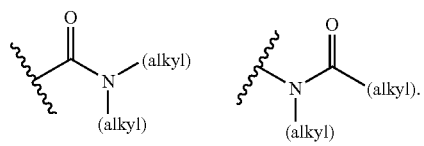

Examples of dialkylcarboxamides include, but are not limited to, N,N-dimethylcarboxamide, N-methyl-N-ethylcarboxamide, N,N-diethylcarboxamide, N-methyl-N-isopropylcarboxamide, and the like.

The term "dialkylsulfonamide" refers to one of the following groups shown below:

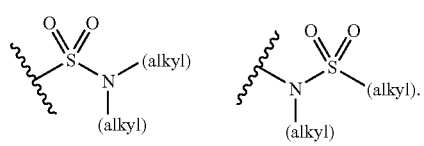

Examples include, but are not limited to, methyl, ethyl, n-propyl, isopropyl, and the like.

The term "dialkylthiocarboxamido" or "dialkylthiocarboxamide" denotes a thioamide substituted by two alkyl radicals, that are the same or different, wherein alkyl has the same definition as described herein. Example dialkylthiocarboxamido groups can be represented by the following groups:

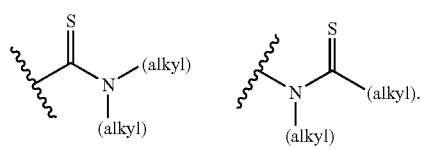

Examples of dialkylthiocarboxamides include, but are not limited to, N,N-dimethylthiocarboxamide, N-methyl-N-ethylthiocarboxamide and the like.

The term "dialkylsulfonylamino" refers to an amino group substituted with two alkylsulfonyl groups as defined herein.

The term "ethynylene" refers to —C≡C—.

The term "formyl" refers to the group —CHO.

The term "guanidine" refers to a group of the following chemical formula:

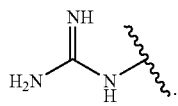

The term "haloalkoxy" denotes —O— substituted by haloalkyl. Examples include, but are not limited to, difluoromethoxy, trifluoromethoxy, 2,2,2-trifluoroethoxy, pentafluoroethoxy, and the like.

The term "haloalkyl" denotes an alkyl group, as defined herein, wherein the alkyl is substituted with one or more halogens. Examples of haloalkyl groups include, but are not limited to, fluoromethyl, difluoromethyl, trifluoromethyl, chlorodifluoromethyl, 2,2,2-trifluoroethyl, pentafluoroethyl and the like.

The term "haloalkylcarboxamide" denotes an alkylcarboxamide group, defined herein, substituted with one or more halogens.

The term "haloalkylsulfinyl" denotes sulfoxide —S(O)— substituted by a haloalkyl radical, wherein the haloalkyl radical has the same definition as described herein. Examples include, but are not limited to, trifluoromethylsulfinyl, 2,2,2-trifluoroethylsulfinyl, 2,2-difluoroethylsulfinyl and the like.

The term "haloalkylsulfonyl" denotes —S(O)$_2$— substituted by a haloalkyl radical, wherein haloalkyl has the same definition as described herein. Examples include, but not limited to, trifluoromethylsulfonyl, 2,2,2-trifluoroethylsulfonyl, 2,2-difluoroethylsulfonyl and the like.

The term "haloalkylthio" denotes —S— substituted by a haloalkyl radical, wherein the haloalkyl has the same meaning as described herein. Examples include, but not limited to, trifluoromethylthio (i.e., CF$_3$S—), 1,1-difluoroethylthio, 2,2,2-trifluoroethylthio and the like.

The term "halogen" or "halo" denotes to a fluoro, chloro, bromo or iodo group.

The term "heteroalkylene" refers to alkylene interrupted or appended by a heteroatom-containing group selected from O, S, S(O), S(O)$_2$ and NH. Some examples include, but not limited to, the groups of the following formulae:

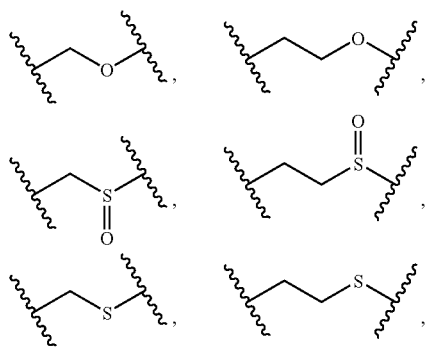

and the like.

The term "heteroaryl" denotes an aromatic ring system that may be a single ring, two fused rings or three fused rings wherein at least one ring carbon is a heteroatom selected from, but not limited to, the group consisting of O, S and N, wherein the N can be optionally substituted with H, O, C$_{1-4}$ acyl or C$_{1-4}$ alkyl. Examples of heteroaryl groups include, but are not limited to, pyridyl, benzofuranyl, pyrazinyl, pyridazinyl, pyrimidinyl, triazinyl, quinoline, benzoxazole, benzothiazole, 1H-benzimidazole, isoquinoline, quinazoline, quinoxaline and the like. In some embodiments, the heteroatom is O, S, NH, examples include, but not limited to, pyrrole, indole, and the like.

The term "heteroarylalkyl" denotes an alkyl group substituted by a heteroaryl group.

The term "heterocyclic" denotes a non-aromatic, cyclic hydrocarbon (i.e., cycloalkyl or cycloalkenyl as defined herein) wherein one or more (e.g., one, two or three) ring carbons are replaced by a heteroatom selected from, but not limited to, the group consisting of O, S, N, wherein the N can be optionally substituted with H, O, C$_{1-4}$ acyl or C$_{1-4}$ alkyl, and ring carbon atoms are optionally substituted with oxo or a sulfido thus forming a carbonyl or thiocarbonyl group. The heterocyclic group can be a 3-, 4-, 5-, 6- or 7-membered ring. Examples of a heterocyclic group include but not limited to aziridin-1-yl, aziridin-2-yl, azetidin-1-yl, azetidin-2-yl, azetidin-3-yl, piperidin-1-yl, piperidin-4-yl, morpholin-4-yl, piperzin-1-yl, piperzin-4-yl, pyrrolidin-1-yl, pyrrolidin-3-yl, [1,3]-dioxolan-2-yl and the like.

The term, "heterocyclicalkyl" denotes an alkyl group substituted by a heterocyclic group.

The term "heterocyclic-carbonyl" denotes a carbonyl group substituted by a heterocyclic group, as defined herein. In some embodiments, a ring nitrogen of the heterocyclic group is bonded to the carbonyl group forming an amide. Examples include, but are not limited to,

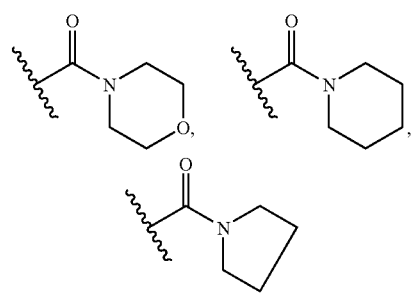

and the like.

In some embodiments, a ring carbon is bonded to the carbonyl group forming a ketone group. Examples include, but are not limited to,

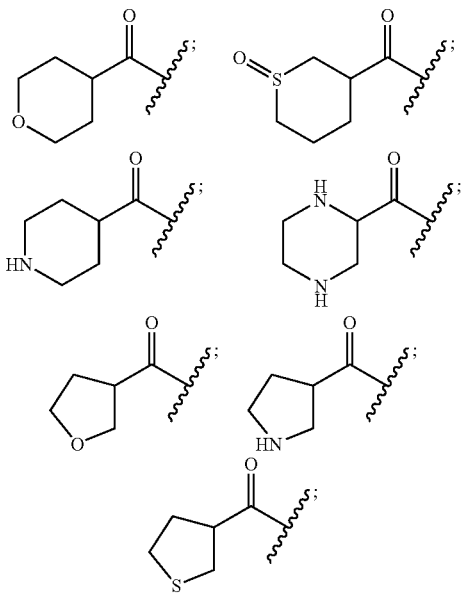

and the like.

The term "heterocyclic-oxy" refers —O— substituted by a heterocyclic group, as defined herein. Examples include the following:

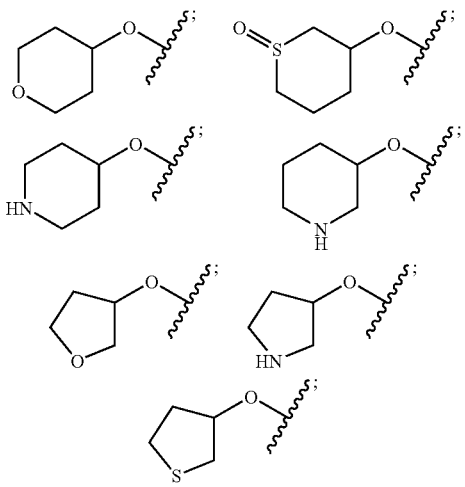

and the like.

The term "heterocyclicsulfonyl" denotes $SO_2$ substituted with a heterocyclic group having a ring nitrogen, where the ring nitrogen is bonded directly to an $SO_2$ group forming an sulfonamide. Examples include, but not limited to,

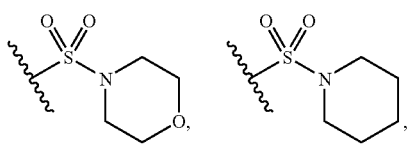

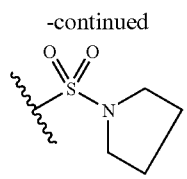

and the like.

The term "hydroxyl" refers to the group —OH.

The term "hydroxylamino" refers to the group —NHOH.

The term "nitro" refers to the group —$NO_2$.

The term "oxo-cycloalkyl" refers to cycloalkyl, as defined herein, wherein one of the ring carbons is replaced with a carbonyl. Examples of oxo-cycloalkyl include, but are not limited to, 2-oxo-cyclobutyl, 3-oxo-cyclobutyl, 3-oxo-cyclopentyl, 4-oxo-cyclohexyl, and the like and represented by the following structures respectively:

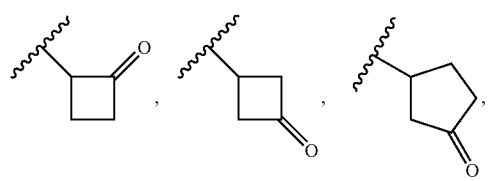

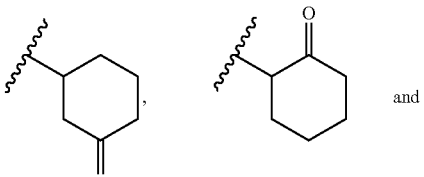

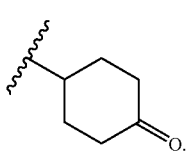

The term "perfluoroalkyl" denotes the group of the formula —$C_nF_{2n+1}$. Examples of perfluoroalkyls include $CF_3$, $CF_2CF_3$, $CF_2CF_2CF_3$, $CF(CF_3)_2$, $CF_2CF_2CF_2CF_3$, $CF_2CF(CF_3)_2$, $CF(CF_3)CF_2CF_3$ and the like.

The term "phenoxy" refers to the group $C_6H_5O$—.

The term "phenyl" refers to the group $C_6H_5$—.

The term "phosphonooxy" refers to a group with the following chemical structure:

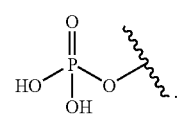

The term "sulfonamide" refers to the group —$SO_2NH_2$.

The term "sulfonic acid" refers to the group —$SO_3H$.

The term "tetrazolyl" refers to the five membered heteroaryl of the following formulae:

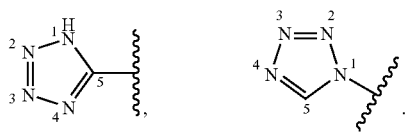

In some embodiments, the tetrazolyl group is further substituted at either the 1 or 5 position, respectively, with a group selected from the group consisting of alkyl, haloalkyl and alkoxy.

The term "thiol" denotes the group —SH.

As used herein, the term "reacting" is used as known in the art and generally refers to the bringing together of chemical reagents in such a manner so as to allow their interaction at the molecular level to achieve a chemical or physical transformation of at least one chemical reagent.

As used herein, the term "substituted" refers to the replacement of a hydrogen moiety with a non-hydrogen moiety in a molecule or group.

For compounds in which a variable appears more than once, each variable can be a different moiety selected from the Markush group defining the variable. For example, where a structure is described having two R groups that are simultaneously present on the same compound; the two R groups can represent different moieties selected from the Markush group defined for R. In another example, when an optionally multiple substituent is designated in the form:

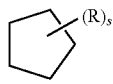

then it is understood that substituent R can occurs number of times on the ring, and R can be a different moiety at each occurrence.

As used herein, the term "leaving group" refers to a moiety that can be displaced by another moiety, such as by nucleophilic attack, during a chemical reaction. Leaving groups are well known in the art and include, for example, halogen including chloro, bromo, iodo, and the like.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

In some embodiments, preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, et al., *Protective Groups in Organic Synthesis*, 3rd. Ed., Wiley & Sons, 1999, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane and hexafluoroethane.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, or t-butyl methyl ether.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable aprotic solvents can include, by way of example and without limitation, tetrahydrofuran (THF), dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include benzene, cyclohexane, pentane, hexane, toluene, cycloheptane, methylcyclohexane, heptane, ethylbenzene, m-, o-, or p-xylene, octane, indane, nonane, or naphthalene.

Supercritical carbon dioxide can also be used as a solvent.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures). "Elevated temperature" refers to temperatures above room temperature (about 25° C.) and "reduced temperature" refers to temperatures below room temperature.

The reactions of the processes described herein can be carried out in air or under an inert atmosphere. Typically, reactions containing reagents or products that are substantially reactive with air can be carried out using air-sensitive synthetic techniques that are well known to the skilled artisan.

In some embodiments, preparation of compounds can involve the addition of acids or bases to effect, for example, catalysis of a desired reaction or formation of salt forms such as acid addition salts.

Example acids can be inorganic or organic acids. Inorganic acids include hydrochloric acid, hydrobromic acid, sulfuric acid, phosphoric acid, and nitric acid. Organic acids include formic acid, acetic acid, propionic acid, butanoic acid, methanesulfonic acid, p-toluene sulfonic acid, benzenesulfonic acid, trifluoroacetic acid, propiolic acid, butyric acid, 2-butynoic acid, vinyl acetic acid, pentanoic acid, hexanoic acid, heptanoic acid, octanoic acid, nonanoic acid and decanoic acid.

Example bases include lithium hydroxide, sodium hydroxide, potassium hydroxide, lithium carbonate, sodium carbonate, and potassium carbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis.

The processes described herein can be stereoselective such that any given reaction starting with one or more chiral reagents enriched in one stereoisomer forms a product that is also enriched in one stereoisomer. The reaction can be conducted such that the product of the reaction substantially retains one or more chiral centers present in the starting materials. The reaction can also be conducted such that the product of the reaction contains a chiral center that is substantially inverted relative to a corresponding chiral center present in the starting materials.

Resolution of racemic mixtures of compounds can be carried out by any of numerous methods known in the art. An example method includes fractional recrystallizaion using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as α-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention can also include all isotopes of atoms occurring in the intermediates or final compounds. Isotopes include those atoms having the same atomic number but different mass numbers. For example, isotopes of hydrogen include tritium and deuterium.

Compounds of the invention can also include tautomeric forms, such as keto-enol tautomers. Tautomeric forms can be in equilibrium or sterically locked into one form by appropriate substitution.

The present invention also includes salt forms of the compounds described herein. Examples of salts (or salt forms) include, but are not limited to, mineral or organic acid salts of basic residues such as amines, alkali or organic salts of acidic residues such as carboxylic acids, and the like. Generally, the salt forms can be prepared by reacting the free base or acid with stoichiometric amounts or with an excess of the desired salt-forming inorganic or organic acid or base in a suitable solvent or various combinations of solvents. Lists of suitable salts are found in *Remington's Pharmaceutical Sciences,* 17th ed., Mack Publishing Company, Easton, Pa., 1985, p. 1418, the disclosure of which is hereby incorporated by reference in its entirety.

Upon carrying out preparation of compounds according to the processes described herein, the usual isolation and purification operations such as concentration, filtration, extraction, solid-phase extraction, recrystallization, chromatography, and the like may be used, to isolate the desired products.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

Preparation of 4,6-Dichloro-5-Methylpyrimidine Intermediate (1)

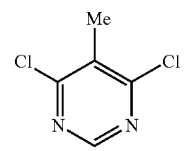

Step 1.

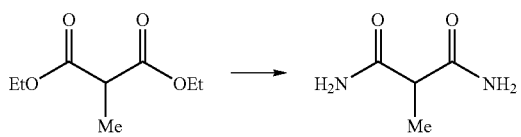

A solution of diethyl-methylmalonate (0.11 mol) in methanol (100 mL) was added to a saturated solution of ammonia in methanol (7N, 200 mL) containing sodium (0.2 g, 0.08 eq) at 0° C. The mixture was allowed to stand in a stoppered flask at room temperature 2-3 days. The separated diamide was collected as a white solid by filtration, washed by methanol and dried.

Step 2.

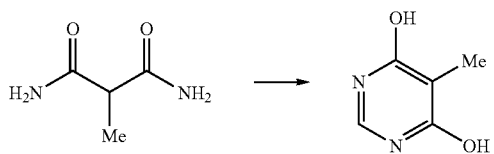

To a solution of Na (1.03 mol, 1.2 eq) in ethanol (2 L) was added diamide from Step 1 (0.86 mol, 1 eq) as a solid. The mixture was heated to reflux and formamide (3.4 mol, 4 eq) was slowly added, the resulting mixture was refluxed for an additional 3 h. The desired compound was filtered at room temperature as a white solid (as a sodium salt), washed by ethanol and dried.

The above solid was dissolved in water, which was acidified to pH=5 using concentrated solution of HCl (12 N). The mixture was stirred at 5° C. for 30 min. The white solid was filtered and dried under vacuum (60% yield).

Step 3.

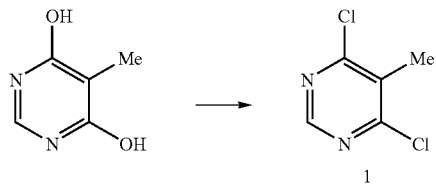

To a mixture of pyrimidine derivative from Step 2 (0.38 mol, 1 eq) in POCl$_3$ (1.9 mol, 174 mL) was slowly added DMF (exothermic reaction, 0.152 mol, 11.7 mL). The resulting mixture was heated to reflux for 3 h, cooled to room temperature and poured into ice/water. The resulting white solid was filtered, washed with water and dried under vacuum (90% yield) to give 4,6-dichloro-5-methylpyrimidine (1).

Example 2

Preparation of 4-Hydroxy-Piperidine-1-Carboxylic Acid Isopropyl Ester Intermediate (2)

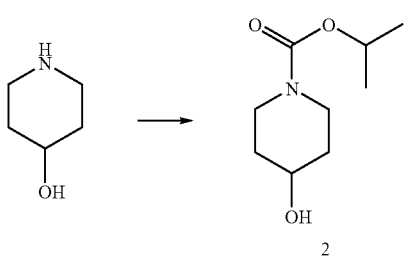

To a stirred mixture of 4-hydroxypiperidine (53.8 g, 1.000 eq), triethylamine (71.8 g, 1.334 equivalents), and ethyl acetate (498.8 g) was added neat isopropyl chloroformate (78.0 g, 1.1966 equivalents) at a rate sufficiently slow to maintain the reaction mixture temperature at 10°-17° C. with reactor jacket cooling. After the addition had been completed, the reaction mixture was stirred at 20° C. for 18 hours. Then water (100 g) was added, and the resulting mixture was stirred for 15 minutes before the phases were separated. The organic phase was washed with two 100-gram-portions of 20 wt % aqueous NaCl by stirring for 15 min at 150 rpm before separating the aqueous wash. After a final wash with water (100 g), the organic phase was concentrated by distillation on a rotary evaporator at reduced pressure to provide product (2) (91.1 g, 92.0% yield) as light amber oil of 96.8% purity by GC. Distillation of this crude product at 117-120° C., 0.3-1.0 torr gave a 95.7% recovery of product (2) as a colorless oil collected at 112°-119° C.

Example 3

Preparation of 4-(6-chloro-5-methyl-pyrimidin-4-yloxy)-piperidine-1-carboxylic acid isopropyl ester intermediate (3)

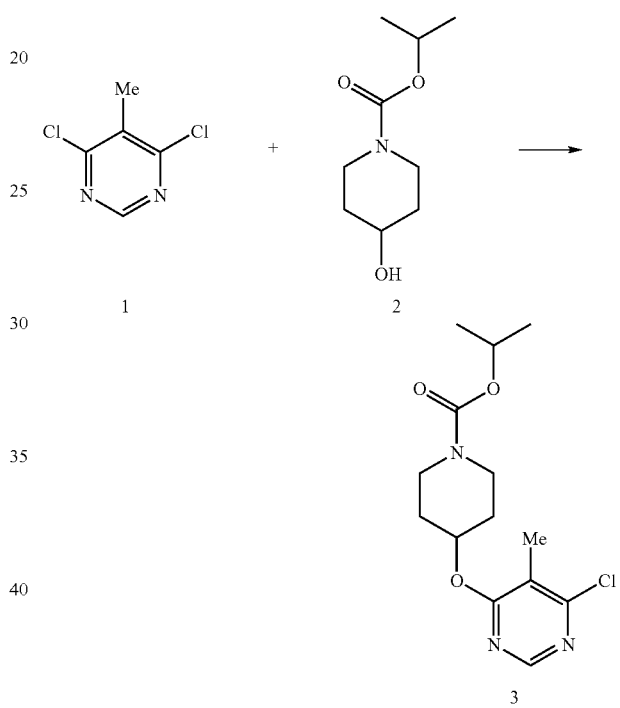

4,6-Dichloro-5-methylpyrimidine (1) (2.4235 Kg, 1.000 equivalents) and 4-hydroxypiperidine-1-carboxylic acid isopropyl ester (2) (2.8182 Kg, 1.012 equivalents) were dissolved in tetrahydrofuran (THF, 25.0028 Kg), and the resulting solution was cooled to −15 to −10° C. To the cold solution, potassium-tert-butoxide in tetrahydrofuran (1 M, 12.6051 Kg, 0.9399 equivalents) was added at a rate sufficiently slow to maintain the reaction mixture below 0° C. with reactor jacket cooling. The reaction mixture was then stirred at about −5° C. for about 2 hours before an additional portion of potassium-tert-butoxide in tetrahydrofuran (1 M, 0.5692 Kg, 0.0424 equivalents) was added to achieve >97% conversion of the pyrimidine after an additional hour of stirring at about −5° C. Most of the solvent was then removed by distillation at 30-65° C., ≦80 torr. Addition of water (19.9681 Kg) to the evaporation residue precipitated the product. Distillative removal of THF was then completed at 30-65° C., ≦80 torr, and the resulting stirred slurry was cooled to 0° C. for an hour. The solids were then collected by suction filtration, washed with water (8.011 Kg, 4° C.), and vacuum dried to constant weight at 50° C., ≦40 torr to provide product (3) (4.491 Kg, 96.3% yield).

Example 4

Preparation of 2-fluoro-4-methanesulfonyl-phenol Intermediate (4)

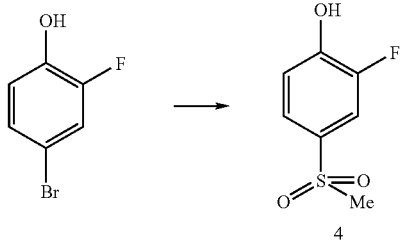

A stirred mixture of sodium methane sulfinic acid (51.0 g, 4.009 equivalents), 4-bromo-2-fluorophenol (23.8 g, 1.000 equivalent), copper(I) trifluoromethanesulfonate benzene complex (6.28 g, 0.1001 equivalents), N,N'-dimethylethylenediamine (DMEDA, 2.2 g, 0.2003 equivalents), and dimethylsulfoxide (DMSO, 104 g) was heated under nitrogen at 130°-135° C. for 18 hours. Substantially all of the DMSO solvent was then removed from the reaction mixture by rotary evaporation at 1 torr with a 120° C. oil bath. To the brown oily distillation residue were added ethyl acetate (90 g) and water (100 g). After the resulting mixture had been heated and agitated to facilitate dissolution of the reaction mixture in the two liquid phases, it was filtered through a coarse sintered glass filter funnel containing a Whatman filter paper disc and 30 g of Celite. Addition of concentrated aqueous HCl (20 g) to the filtrate lowered the pH of the aqueous phase to less than 3. The phases were separated, and the aqueous phase was extracted two more times with ethyl acetate (90 g each). The combined organic phases were extracted with three 100-gram-portions of 1 M aqueous NaOH to extract the sodium salt of the phenoxide product into the aqueous phase. The aqueous phases were combined, acidified with cooling and concentrated aqueous HCl (40 g) to a pH less than 3, and then extracted with four 90-gram-portions of ethyl acetate to return the product as the free phenol to the organic phase. The organic phases were combined, dried over magnesium sulfate (15 grams), filtered, and concentrated by rotary evaporation at reduced pressure to provide product (4) (16.6 g, 70% yield) as a clear orange to brown oil, which solidified on standing.

Example 5

Preparation of 4-[6-(2-fluoro-4-methanesulfonyl-phenoxy)-5-methyl-pyrimidin-4-yloxy]-piperidine-1-carboxylic Acid Isopropyl Ester (5)

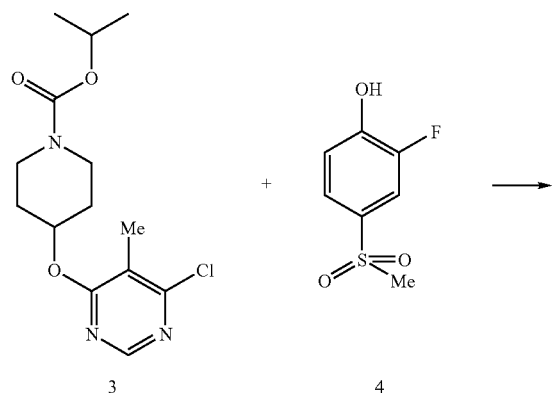

-continued

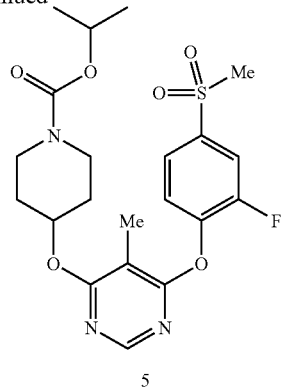

2-Fluoro-4-methanesulfonylphenol (4) (1.9863 Kg, 1.000 equivalent) and 4-(6'-chloro-5'-methylpyrimidin-4'-yloxypiperidine)-1-carboxylic acid isopropyl ester (3) (3.3656 Kg, 1.027 equivalents) were dissolved in dimethylsulfoxide (DMSO, 7.0160 Kg). To the resulting solution, tetrabutylammonium iodide promoter (2.5243 Kg, 0.6544 equivalents) and potassium carbonate (1.7422 Kg, 1.207 equivalents) were added. The reaction mixture was then stirred and heated at 130°-135° C. internal temperature for about 24 hours, at which point conversion of phenol (4) to product (5) was >93%. The reaction mixture was then cooled to 50°-60° C. and, with the assistance of additional DMSO (0.5050 Kg), added to water (36.1206 Kg) maintained at 25°-35° C. throughout the addition. After the resulting slurry had been stirred at about 20° C. for several hours, the precipitated solids were filtered, washed with water (8.1264 Kg, 20° C.), and recrystallized from isopropyl alcohol (18.7195 Kg) by dissolution at 80° C. and cooling to 2° C. The recrystallization mixture was stirred at 2° C. for two hours and then filtered. The filtered solid product was washed with a 2° C. mixture of isopropanol (6.9792 Kg) and water (3.0329 Kg) and then recrystallized a second time from isopropanol (15.8899 Kg, 80° C.). After having been cooled to and stirred at 2° C. for two hours, the recrystallization mixture was filtered. The filtered solid product was washed with a 2° C. mixture of isopropanol (5.8689 Kg) and water (2.590 Kg) and dried to constant weight at 50° C., ≦40 torr to provide product (5) (3.8937 Kg, 79.75% yield).

Example 6

Preparation of 4-[6-(2-fluoro-4-methanesulfonyl-phenoxy)-5-methyl-pyrimidin-4-yloxy]-piperidine-1-carboxylic Acid Isopropyl Ester (5)

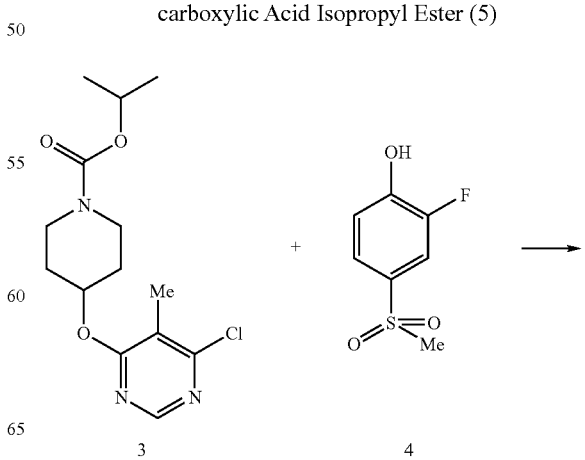

-continued

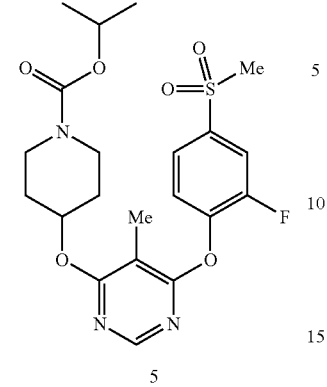

5

2-Fluoro-4-methanesulfonyl-phenol (4) (1.33 g, 7.01 mmol) and 4-(6-chloro-5-methyl-pyrimidin-4-yloxy)-piperidine-1-carboxylic acid isopropyl ester (3) (2.00 g, 6.39 mmol) were dissolved in DMSO (10 mL). To the resulting solution, potassium iodide (0.21 g, 1.27 mmol) and potassium carbonate (0.97 g, 7.01 mmol) were added. The resulting mixture was heated to 130° C. and stirred overnight. The crude was cooled to room temperature, poured into ice water (150 mL) and stirred for 2 h. The precipitate was filtered, washed twice with water (2×10 mL) and dried at 60° C. in a vacuum oven (2.74 g, 91%). The desired product was recrystallized from isopropanol (10 mL) to afford 2.39 g of the title compound (80%).

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

What is claimed is:

1. A process for preparing a compound of Formula I:

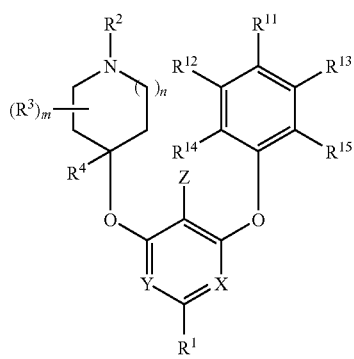

I wherein:

X is N and Y is N or $CR^8$; or

X is N or $CR^7$ and Y is N;

Z is $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, $C_{1-2}$ alkylamino, $C_{2-4}$ dialkylamino, carbamimidoyl, carbo-$C_{1-6}$-alkoxy, carboxamide, carboxy, cyano, $C_{3-7}$ cycloalkyl, $C_{4-8}$ diacylamino, $C_{2-6}$ dialkylcarboxamide, $C_{2-6}$ dialkylthiocarboxamide, $C_{2-6}$ dialkylsulfonamide, $C_{2-6}$ dialkylsulfonylamino, formyl, $C_{1-4}$ haloalkoxy, haloalkyl, $C_{1-4}$ haloalkylcarboxamide, $C_{1-4}$ haloalkylsulfinyl, $C_{1-4}$ haloalkylsulfonyl, $C_{1-4}$ haloalkylthio, halogen, aryl, heteroaryl, heterocycloalkyl, hydroxyl, hydroxycarbamimidoyl, hydroxylamino, nitro, or tetrazolyl; wherein said $C_{1-8}$ alkyl, $C_{3-7}$ cycloalkyl, and heterocycloalkyl are each optionally substituted with 1, 2, 3 or 4 groups selected from $C_{1-5}$ acyl, $C_{1-5}$ acyloxy, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, alkylthio, $C_{1-4}$ alkylureyl, amino, $C_{1-2}$ alkylamino, $C_{2-4}$ dialkylamino, carbo-$C_{1-6}$-alkoxy, carboxamide, carboxy, cyano, formyl, $C_{1-4}$ haloalkoxy, $C_{1-4}$ haloalkylsulfinyl, $C_{1-4}$ haloalkylsulfonyl, $C_{1-4}$ haloalkylthio, halogen, hydroxyl, hydroxylamino, and nitro;

$R^1$ is H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-7}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, or hydroxyl;

$R^2$ is —$R^{22}$, —$CR^{23}R^{24}C(O)$—$R^{22}$, —$C(O)CR^{23}R^{24}$—$R^{22}$, —$C(O)$—$R^{22}$, —$CR^{23}R^{24}C(O)NR^{25}$—$R^{22}$, —$NR^{25}C(O)CR^{23}R^{24}$—$R^{22}$, —$C(O)NR^{23}$—$R^{22}$, —$NR^{23}C(O)$—$R^{22}$, —$C(O)O$—$R^{22}$, —$OC(O)$—$R^{22}$, —$C(S)$—$R^{22}$, —$C(S)NR^{23}$—$R^{22}$, —$NR^{23}C(S)$—$R^{22}$, —$C(S)O$—$R^{22}$, —$OC(S)$—$R^{22}$, —$CR^{23}R^{24}$—$R^{22}$, or —$S(O)_2$—$R^{22}$;

$R^3$ is $C_{1-3}$ alkyl, $C_{1-4}$ alkoxy, carboxy, cyano, $C_{1-3}$ haloalkyl, or halogen;

$R^4$ is H, $C_{1-8}$ alkyl or $C_{3-7}$ cycloalkyl, wherein said $C_{1-8}$ alkyl is optionally substituted with $C_{1-4}$ alkoxy, $C_{3-7}$ cycloalkyl, or heteroaryl;

$R^7$ and $R^8$ are each, independently, H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-7}$ cycloalkyl, $C_{2-6}$ dialkylcarboxamide, $C_{7-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, or hydroxyl;

$R^{11}$ is $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, arylsulfonyl, carbamimidoyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, $C_{2-6}$ dialkylthiocarboxamide, guanidinyl, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocycloalkyl, heterocycloalkyl-oxy, heterocycloalkylsulfonyl, heterocycloalkyl-carbonyl, heteroaryl, heteroarylcarbonyl, hydroxyl, nitro, $C_{4-7}$ oxo-cycloalkyl, phenoxy, phenyl, sulfonamide, sulfonic acid, or thiol; and wherein said $C_{1-5}$ acyl, $C_{1-6}$ acylsulfonamide, $C_{1-4}$ alkoxy, $C_{1-6}$ alkyl, $C_{1-4}$ alkylamino, $C_{1-6}$ alkylsulfonamide, $C_{1-4}$ alkylsulfonyl, $C_{1-4}$ alkylthio, arylsulfonyl, carbamimidoyl, $C_{2-6}$ dialkylamino, heterocycloalkyl, heterocycloalkyl-carbonyl, heteroaryl, phenoxy and phenyl are each optionally substituted with 1 to 5 substituents selected independently from $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro, phenyl, and phosphonooxy, wherein said $C_{1-7}$ alkyl and $C_{1-4}$ alkylcarboxamide are each optionally substituted with 1 to 5 substituents selected from $C_{1-4}$ alkoxy and hydroxy;

$R^{12}$, $R^{13}$, $R^{14}$, and $R^{15}$ are each, independently, H, $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, or nitro;

$R^{22}$ is H, $C_{1-8}$ alkyl, $C_{3-7}$ cycloalkyl, phenyl, heteroaryl, or heterocyclic each optionally substituted with 1 to 5 substituents selected from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, haloalkylsulfonyl, $C_{1-4}$ haloalkyl, $C_{1-4}$ haloalkylthio, halogen, heteroaryl, heterocyclic, hydroxyl, hydroxylamino, nitro, phenyl, phenoxy, and sulfonic acid, wherein said $C_{1-7}$ alkyl, heteroaryl, phenyl and phenoxy are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-4}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino, and nitro;

$R^{23}$, $R^{24}$ and $R^{25}$ are each, independently, H or $C_{1-8}$ alkyl;
n is 0 or 1; and
m is 0, 1, 2, 3, or 4;

wherein said process comprises reacting a compound of Formula II:

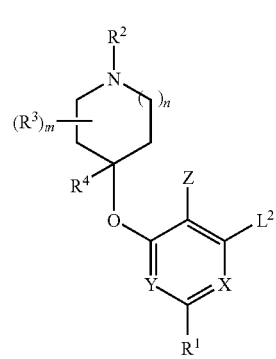

wherein $L^2$ is a leaving group, with compound of Formula III:

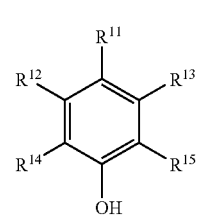

in the presence of a base and an iodide salt, thereby forming the compound of Formula I.

2. The process of claim 1 wherein said salt is a tetrasubstituted ammonium iodide salt.

3. The process of claim 1 wherein said base is an alkali metal amide, alkali metal hydride, alkali metal carbonate, or an alkali metal hydrogencarbonate.

4. The process of claim 1 wherein said base is $K_2CO_3$.

5. The process of claim 1 wherein said reacting is carried out at elevated temperature.

6. The process of claim 1 wherein said reacting is carried out at a temperature of about 120 to about 140° C.

7. The process of claim 1 wherein said reacting is carried out in a solvent.

8. The process of claim 7 wherein said solvent comprises DMSO.

9. The process of claim 1 wherein $L^2$ is halo.

10. The process of claim 1 wherein $L^2$ is Cl.

11. The process of claim 1 wherein both X and Y are N.

12. The process of claim 1 wherein Z is $C_{1-5}$ acyl, $C_{1-5}$ acyloxy, $C_{2-6}$ alkenyl, $C_{1-4}$ alkoxy, $C_{1-8}$ alkyl, $C_{2-6}$ alkynyl, formyl, $C_{1-4}$ haloalkoxy, $C_{1-4}$ haloalkyl, halogen, hydroxyl, or nitro.

13. The process of claim 1 wherein Z is methyl.

14. The process of claim 1 wherein $R^1$ is H.

15. The process of claim 1 wherein $R^2$ is —C(O)O—$R^{22}$ and $R^{22}$ is methyl, ethyl, prop-1-yl, or prop-2-yl.

16. The process of claim 1 wherein $R^2$ is —C(O)O—$R^{22}$ and $R^{22}$ is prop-2-yl.

17. The process of claim 1 wherein $R^4$ is H.

18. The process of claim 1 wherein n is 1.

19. The process of claim 1 wherein m is 0.

20. The process of claim 1 wherein $R^{11}$ is $C_{1-4}$ alkylsulfonyl.

21. The process of claim 1 wherein $R^{11}$ is methylsulfonyl.

22. The process of claim 1 wherein $R^{12}$, $R^{13}$, $R^{14}$, and $R^{15}$ are each, independently, H or halogen.

23. The process of claim 1 wherein $R^{15}$ is F.

24. The process of claim 1 wherein $R^{11}$ is $C_{1-4}$ alkylsulfonyl; $R^{12}$, $R^{13}$, and $R^{14}$ are each H; and $R^{15}$ is halogen.

25. The process of claim 1 wherein:
X is N;
Y is N;
Z is methyl;
$R^1$ is H;
$R^2$ is —C(O)O—$R^{22}$;
$R^4$ is H;
$R^{11}$ is methylsulfonyl;
$R^{12}$, $R^{13}$, and $R^{14}$ are each H;
$R^{15}$ is F;
$R^{22}$ is prop-2-yl;
n is 1; and
m is 0.

26. The process of claim 1 wherein said compound of Formula II is prepared by:
a) combining a compound of Formula IV:

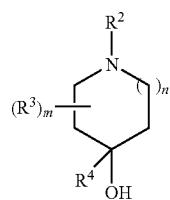

with a compound of Formula V:

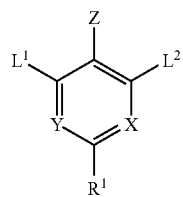

wherein $L^1$ is a leaving group, to form a mixture; and
b) adding a base to said mixture, thereby forming the compound of Formula II.

27. The process of claim 26 wherein said base is $C_{1-6}$ alkoxide salt, alkali metal amide, alkali metal hydride, alkali metal carbonate, or an alkali metal hydrogencarbonate.

28. The process of claim 26 wherein said base is potassium t-butoxide.

29. The process of claim 26 wherein said combining and adding are carried out in a solvent.

30. The process of claim 29 wherein said solvent comprises tetrahydrofuran.

31. The process of claim 26 wherein said adding is carried out at a temperature below about 10° C.

32. The process of claim 26 wherein $L^1$ is halo.

33. The process of claim 26 wherein $L^1$ is Cl.

34. The process of claim 1 wherein X is N.

35. The process of claim 1 wherein Y is N.

36. The process of claim 1 wherein said salt is tetrabutylammonium iodide.

37. The process of claim 1 wherein said reacting is carried out at a temperature of about 100 to about 150° C.

38. The process of claim 1 wherein said reacting is carried out at a temperature of about 130 to about 135° C.

39. The process of claim 1 wherein Z is $C_{1-8}$ alkyl.

40. The process of claim 1 wherein $R^2$ is —C(O)O—$R^{22}$.

41. The process of claim 1 wherein:
X is N;
Y is N;
Z is $C_{1-5}$ acyl, $C_{1-5}$ acyloxy, $C_{2-6}$ alkenyl, $C_{1-4}$ alkoxy, $C_{1-8}$ alkyl, $C_{2-6}$ alkynyl, formyl, $C_{1-4}$ haloalkoxy, $C_{1-4}$ haloalkyl, halogen, hydroxyl, or nitro;
$R^1$ is H;
$R^2$ is —C(O)O—$R^{22}$;
$R^4$ is H;
$R^{11}$ is $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, or $C_{1-4}$ alkylsulfonyl;
$R^{12}$, $R^{13}$, $R^{14}$, and $R^{15}$ are each, independently, H, $C_{2-6}$ alkenyl, $C_{1-4}$ alkoxy, $C_{1-8}$ alkyl, $C_{2-6}$ alkynyl, cyano, halogen, $C_{1-4}$ haloalkoxy, $C_{1-4}$ haloalkyl, hydroxyl or nitro;
n is 1; and
m is 0 or 1.

42. The process of claim 1 wherein:
X is N;
Y is N;
Z is $C_{1-8}$ alkyl;
$R^1$ is H;
$R^2$ is —C(O)O—$R^{22}$;
$R^4$ is H;
$R^{11}$ is $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, or $C_{1-4}$ alkylsulfonyl;
$R^{12}$, $R^{13}$, and $R^{14}$ are each H;
$R^{15}$ is $C_{2-6}$ alkenyl, $C_{1-4}$ alkoxy, $C_{1-8}$ alkyl, $C_{2-6}$ alkynyl, cyano, halogen, $C_{1-4}$ haloalkoxy, $C_{1-4}$ haloalkyl, hydroxyl, or nitro;
n is 1; and
m is 0 or 1.

43. The process of claim 1 wherein:
X is N;
Y is N;
Z is $C_{1-8}$ alkyl;
$R^1$ is H;
$R^2$ is —C(O)O—$R^{22}$;
$R^4$ is H;
$R^{11}$ is $C_{1-4}$ alkylsulfinyl or $C_{1-4}$ alkylsulfonyl;
$R^{12}$, $R^{13}$, and $R^{14}$ are each H;
$R^{15}$ is $C_{2-6}$ alkenyl, $C_{1-4}$ alkoxy, $C_{1-8}$ alkyl, $C_{2-6}$ alkynyl, cyano, halogen, $C_{1-4}$ haloalkoxy, $C_{1-4}$ haloalkyl, hydroxyl, or nitro;
$R^{22}$ is $C_{1-4}$ alkyl;
n is 1; and
m is 0.

* * * * *